(12) United States Patent
Stone et al.

(10) Patent No.: US 10,500,167 B2
(45) Date of Patent: Dec. 10, 2019

(54) DROPLET-EMBEDDED MICROFIBERS, AND METHODS AND DEVICES FOR PREPARING AND USING SAME

(71) Applicant: TRUSTEES OF PRINCETON UNIVERSITY, Princeton, NJ (US)

(72) Inventors: Howard A. Stone, Princeton, NJ (US); Janine K. Nunes, Plainsboro, NJ (US); Eujin Um, Ulsan (KR); Tamara Pico, Cambridge, MA (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 3 days.

(21) Appl. No.: 15/833,528

(22) Filed: Dec. 6, 2017

(65) Prior Publication Data

US 2018/0092861 A1 Apr. 5, 2018

Related U.S. Application Data

(63) Continuation of application No. 14/680,710, filed on Apr. 7, 2015, now abandoned.
(Continued)

(51) Int. Cl.
*A61K 9/16* (2006.01)
*A61K 31/085* (2006.01)
(Continued)

(52) U.S. Cl.
CPC .......... *A61K 31/085* (2013.01); *A61K 9/0092* (2013.01); *A61K 9/5026* (2013.01);
(Continued)

(58) Field of Classification Search
CPC . C08K 5/17; A61K 9/10; A61K 9/113; A61K 9/14; A61K 9/1277; A61K 9/16; A61K 9/1682
See application file for complete search history.

(56) References Cited

U.S. PATENT DOCUMENTS 3,943,949 A   3/1976 Ashton et al.
5,577,147 A   11/1996 Arroyo et al.
(Continued)

OTHER PUBLICATIONS

Oh, H. et al., Hydrodynamic Micro-Encapsulation of Aqueous Fluids and Cells Via 'On the Fly' Photopolymerization, J. ournal of Micromechanics and Microengineering, 2006, pp. 285-291, vol. 16.
(Continued)

*Primary Examiner* — Micah Paul Young
(74) *Attorney, Agent, or Firm* — Meagher Emanuel Laks Goldberg & Liao, LLP

(57) ABSTRACT

The invention includes microfluidic methods and devices that allow for the continuous production of microfibers with embedded droplets aligned along the length of the fiber at specific positions. The invention allows for formation of single or multiple emulsions within a fiber. The various phases comprised within the fiber can vary in terms of in terms of hydrophobic/hydrophilic character, solid/fluid, or gel crosslink density, which allows for the introduction of heterogeneous microenvironments within the fiber, each of which with distinct solubility characteristics, permeability, and mechanical properties. Various compounds and materials can be encapsulated in the different microcompartments of the fiber for storage and delivery applications, as well as to provide multifunctionality to the fiber structure. The disclosed structures have a broad range of potential applications, for example as engineered substrates with controlled release profiles of multiple compounds for tissue engineering (such as a tissue scaffold, for example) and bioengineering applications.

35 Claims, 13 Drawing Sheets

Related U.S. Application Data

(60) Provisional application No. 61/976,599, filed on Apr. 8, 2014.

(51) Int. Cl.

| | | |
|---|---|---|
| *A61K 49/00* | (2006.01) | |
| *A61K 9/00* | (2006.01) | |
| *A61K 9/50* | (2006.01) | |
| *A61L 27/50* | (2006.01) | |
| *A61L 27/54* | (2006.01) | |
| *A61L 27/58* | (2006.01) | |

(52) U.S. Cl.
CPC ...... *A61K 49/0043* (2013.01); *A61K 49/0093* (2013.01); *A61L 27/50* (2013.01); *A61L 27/54* (2013.01); *A61L 27/58* (2013.01); *A61L 2300/62* (2013.01)

(56) References Cited

U.S. PATENT DOCUMENTS

| | | | | |
|---|---|---|---|---|
| 2002/0058332 | A1* | 5/2002 | Quake | G01N 15/1459 |
| | | | | 435/288.5 |
| 2012/0108721 | A1* | 5/2012 | Mazutis | B01F 3/0807 |
| | | | | 524/236 |
| 2013/0202888 | A1 | 8/2013 | Abouraddy et al. | |
| 2013/0280307 | A1 | 10/2013 | Fullana et al. | |

OTHER PUBLICATIONS

Kang, E. et al., Digitally tunable physicochemical coding of material composition and topography in continuous microfibres, Nature Materials, 2011, pp. 877-883, vol. 10.

Yu, Y et al., Flexible Fabrication of Biomimetic Bamboo-Like Hybrid Microfibers, Advanced Materials, 2014, pp. 2494-2499, vol. 26.

Jun, Y et al., Microfluidic spinning of micro- and nano-scale fibers for tissue engineering, Lab on a Chip, The Royal Society of Chemistry, pp. 2145-2160, Jul. 7, 2014, vol. 14, No. 13.

Li, D. et al., Electrospinning of Nanofibers: Reinventing the Wheel?, Advanced Materials, pp. 1151-1170, Jul. 19, 2004, vol. 16, No. 14.

Burger, C. et al., Nanofibrous Materials and Their Applications, Annual Review of Materials Research, 2006, pp. 333-368, vol. 36.

Onoe, H. et al., Metre-long cell-laden microfibres exhibit tissue morphologies and functions, Nature Materials, Mar. 31, 2013, pp. 584-590, vol. 12.

Yamada, M. et al., Controlled formation of heterotypic hepatic micro-organoids in anisotropic hydrogel microfibers for long-term preservation of liver-specific functions, Biomaterials, 2012, pp. 8304-8315, vol. 33.

Yamada, M. et al., Microfluidic synthesis of chemically and physically anisotropic hydrogel microfibers for guided call growth and networking, Soft Matter, 2012, pp. 3122-3130, vol. 8.

Zahedi, P. et al., A review on wound dressings with an emphasis on electrospun nanofibrous polymeric bandages, Polymers Advanced Technologies, 2010, pp. 77-95, vol. 21.

Zilberman, M. et al., Gentamicin-eluting bioresorbable composite fibers for would healing applications, Journal of Biomedical Materials Research Part A, 2009, pp. 654-666.

Nardi, A. et al., Phenol Biodegradation by Corynebacterium glutamicum Encapsulated in Electrospun Fibers, Journal of Environmental Protection, 2012, pp. 164-168, vol. 3.

Sinha-Ray, S. et al., Encapsulation of self healing materials by electrospinning, emulsion electrospinning, solution blowing and intercalation, Journal of Materials Chemistry, 2012, pp. 9138-9146, vol. 22.

Arecchi, A. et al., Electrospinning of Poly (vinyl alcohol) Nanofibers Loaded with Hexadecane Nanodroplets, Journal of Food Science, 2010, pp. N80-N88, vol. 75, No. 6, Institute of Food Technologies.

Sultana, K. et al., Encapsulation of probiotic bacteria with alginate-starch and evaluation of survival in simulated gastrointestinal conditions and in yoghurt, International Journal of Food Microbiology, 2000, pp. 47-55, vol. 62.

Dong, B. et al., Encapsulation of Multiple Biological Compounds Within a Single Electrospun Fiber, 2009, pp. 1508-1512, vol. 5, No. 13.

Sanders, E. et al., Two-Phase Electrospinning from a Single Electrified Jet: Microencapsulation of Aqueous Reservoirs in Poly (ethylene-co-vinyl acetate) Fibers, Macromolecules, 2003, pp. 3803-3805, vol. 36.

Sy, J. et al., Emulsion as a Means of Controlling Electrospinning of Polymers, Advanced Materials, 2009, pp. 1814-1819, vol. 21.

Korehei, R et al., Incorporation of T4 bacteriophage in electrospun fibres, Journal of Applied Microbiology, pp. 1425-1434, 2013, vol. 114.

Kriegel, C. et al., Nanofibers as Carrier Systems for Antimicrobial Microemulsions, Langmuir, 2009, pp. 1154-1161, vol. 25.

* cited by examiner (a) 10% eugenol   (b) 20% eugenol 3 hours 6 hours 15 hours

Fibers in sodium citrate (a)

(b)

(c) ### Fibers in ethanol

| $Q_{oil\ phase}$ ($\mu L\ hr^{-1}$) | $Q_{inner\ alginate\ phase}$ ($\mu L\ hr^{-1}$) | Number of alginate particles per oil drop |
|---|---|---|
| 5 | 0.5 | 2 |
| 20 | 5 | 1 |
| 40 | 16 | 4 |
| 60 | 20 | 6 |
| 70 | 23 | 10 |
| 90 | 29 | 13 |
| 110 | 42 | started wetting |

DROPLET-EMBEDDED MICROFIBERS, AND METHODS AND DEVICES FOR PREPARING AND USING SAME

CROSS-REFERENCE TO RELATED APPLICATIONS

The present application is a continuation of U.S. application Ser. No. 14/680,710, filed Apr. 7, 2015, which claims priority under 35 U.S.C. § 119(e) to U.S. Provisional Patent Application No. 61/976,599, filed Apr. 8, 2014, which is incorporated herein by reference in its entirety.

STATEMENT REGARDING FEDERALLY SPONSORED RESEARCH OR DEVELOPMENT

This invention was made with government support under grant number FA9550-12-1-0368 awarded by the Air Force Office of Scientific Research (AFOSR). The government has certain rights in the invention.

BACKGROUND

One-dimensional, high aspect ratio flexible structures, such as micro- and nanofibers, offer various advantages. In one aspect, the properties, geometry and composition of micro- and nanofibers can be controlled at the micron and sub-micron length scales (Jun, et al., 2014, Lab Chip 14:2145; Li & Xia, 2004, Adv. Mater. 16:1151). In another aspect, these fibers can be used at larger length scales to create complex assemblies and three-dimensional architectures, such as meshes and textiles (Burger, et al., 2006, Annu. Rev. Mater. Res. 36:333; Onoe, et al., 2013, Nat. Mater. 12:584).

Approaches that add versatility and functionality to micro- and nanofibers would allow for the creation of 'smart' materials useful within life science and materials science applications. The utilization of composite structures is a common approach to add such multifunctionality. Composite fiber structures with tailored volume fractions of components, precise spatial control, and controlled chemistry and loading of cargo are appealing for many applications, such as scaffolds for the spatial control of cellular microenvironments in tissue engineering (Yamada, et al., 2012, Soft Matter 8:3122; Yamada, et al., 2012, Biomaterials 33:8304), local delivery of therapeutics for wound healing applications (Zahedi, et al., 2010, Polymer. Adv. Tech. 21:77; Zilberman, et al., 2009, J. Biomed. Mater. Res. A 89A:654), immobilization and protection of bacteria in bioreactors (Nardi, et al., 2012, J. Environ. Prot. 3:164), self-healing composite materials for load bearing applications (Sinha-Ray, et al., 2012, J. Mater. Chem. 22:9138), and food science (Arecchi, et al., 2010, J. Food Sci. 75:N80; Sultana, et al., Int. J. Food Microbiol. 62:47).

An exemplary approach for generating composite fibers is to use an emulsion as the pre-fiber solution (Arecchi, et al., 2010, J. Food Sci. 75:N80; Sultana, et al., Int. J. Food Microbiol. 62:47; Dong, et al., 2009, Small 5:1508; Sanders, et al., 2003, Macromolecules 36:3803; Sy, et al., 2009, Adv. Mater. 21:1814; Korehei & Kadla, 2013, J. Appl. Microbiol. 114:1425; Kriegel, et al., 2009, Langmuir 25:1154). Using this process, cargos such as proteins, antimicrobial compounds, and self-healing compounds have been incorporated into electrospun nanofibers. To avoid the mechanical stresses associated with bulk emulsification techniques on fragile cargo, as are results of use of homogenizers and ultrasonication, other techniques have been developed, such as compound-jet electrospinning, coaxial electrospinning, thermally induced in-fiber emulsification of an extruded core-shell fiber, coaxial microfluidics, microfluidics incorporating stratified flows for mosaicked fibers, and valve-based microfluidics for coded fibers. These techniques can generate micro/nanofibers containing various cargos, including cells, drugs, and proteins.

Some methods for producing composite fibers, such as using bulk emulsification, are relatively simple to execute, but lack the spatial control desired for advanced applications. Others, while efficient at fabricating fibers with complex morphologies and a high level of spatial control, rely on complex device designs and externally controlled actuation.

There is a need in the art for novel methods and devices for preparing multi-compartment nano- and microfibers comprising embedded droplets along the length of the fibers. In certain aspects, such methods and devices should allow for control over the spacing of the embedded droplets along the length of the fiber. In other aspects, such methods and devices should allow for encapsulation of components in distinct microcompartments. This provides controlled storage, dissolution and/or delivery of the components. The present invention meets this need.

BRIEF SUMMARY

The invention provides microfibers comprising a matrix material, and microfibers comprising an outer matrix material and an inner matrix material. The invention further provides microfluidic devices, and methods of preparing microfibers using same. The invention further provides systems comprising a microfluidic device and one or more fluid reservoirs. The invention further provides methods of physically displacing a microfiber in accordance with the present invention.

In certain embodiments, the microfiber further comprises a plurality of droplets embedded in the matrix material along a length thereof; wherein each one of the plurality of droplets independently comprises a single fluid; wherein each one of the plurality of droplets is insoluble in the matrix material of the microfiber; and wherein, if the matrix material of the microfiber is hydrophilic, the matrix material is prepared from a precursor using at least one method selected from the group consisting of polymerization, solvent extraction and covalent crosslinking.

In certain embodiments, the microfiber further comprises a plurality of droplets embedded in the matrix material along the length thereof; wherein each one of the plurality of droplets independently comprises an emulsion comprising a first droplet phase within a second droplet phase; and wherein the matrix material of the microfiber is insoluble in the second droplet phase of each one of the plurality of droplets.

In certain embodiments, the outer matrix material and the inner matrix material span the length of the microfiber; wherein the inner matrix material is embedded in the outer matrix material; wherein the microfiber further comprises a plurality of droplets embedded in the inner matrix material along the length thereof; and wherein the inner matrix material of the microfiber is insoluble in each one of the plurality of droplets and in the outer matrix material.

In certain embodiments, the matrix material has a composition that does not vary substantially along a length of the microfiber. In other embodiments, the matrix material has a composition that varies along a length of the microfiber. In yet other embodiments, each one of the plurality of the droplets has a like composition. In yet other embodiments, at least one of the plurality of droplets has a first composition, and at least one other of the plurality of droplets has a second composition, the first composition being different from the second composition.

In certain embodiments, the matrix material further comprises at least one agent selected from the group consisting of a cell, tissue, filler, therapeutic drug, chemoattractant, biocide, ion, peptide, protein, nucleic acid, magnetic compound, and detectable probe. In other embodiments, at least one of the plurality of droplets further comprises at least one agent selected from the group consisting of a cell, tissue, filler, therapeutic drug, chemoattractant, biocide, ion, peptide, protein, nucleic acid, magnetic compound, and detectable probe. In yet other embodiments, at least one selected from the group consisting of the matrix material and at least one of the plurality of droplets comprises a magnetic compound.

In certain embodiments, the matrix material of the microfiber is hydrophobic and the single fluid of the droplet is hydrophilic. In other embodiments, the matrix material of the microfiber is hydrophilic and the single fluid of the droplet is hydrophobic. In yet other embodiments, the matrix material of the microfiber is hydrophilic and the second droplet phase of each one of the plurality of droplets is hydrophobic. In yet other embodiments, the matrix material of the microfiber is hydrophobic and the second droplet phase of each one of the plurality of droplets is hydrophilic. In yet other embodiments, the first droplet phase of at least one of the plurality of droplets comprises a solid.

In certain embodiments, the matrix material comprises a first agent and at least one of the plurality of droplets comprises a second agent, the second agent having distinct solubility or distinct chemical compatibility from the first agent. In other embodiments, within at least one of the plurality of droplets the first droplet phase comprises a first agent and the second droplet phase comprises a second agent, the second agent having at least one property selected from the group consisting of solubility and chemical compatibility that is distinct from that of the first agent. In yet other embodiments, the matrix material of the microfiber is biodegradable.

In certain embodiments, the outer and inner matrix materials are coaxially aligned within the microfiber. In other embodiments, the radius of the inner matrix material is substantially constant along a length of the microfiber. In yet other embodiments, the radius of the outer matrix material is substantially constant along a length of the microfiber. In yet other embodiments, at least one selected from the group consisting of the outer matrix material and the inner matrix material further comprises at least one agent selected from the group consisting of a cell, tissue, filler, therapeutic drug, chemoattractant, biocide, ion, peptide, protein, nucleic acid, magnetic compound, and detectable probe.

In certain embodiments, the outer matrix material is hydrophilic, the inner matrix material is hydrophobic, and each one of the plurality of droplets is hydrophilic. In other embodiments, the outer matrix material is hydrophobic, the inner matrix material is hydrophilic, and each one of the plurality of droplets is hydrophobic.

In certain embodiments, the microfluidic device comprises a first microfluidic duct for delivering a first fluid; a second microfluidic duct for delivering a second fluid, the second fluid being immiscible with the first fluid; wherein the first microfluidic duct opens into the second microfluidic duct and forms a first fluidic junction therewith; a third microfluidic duct that is in fluid communication with the first fluidic junction and is wettable by the second fluid; a fourth microfluidic duct for delivering a third fluid; wherein the third microfluidic duct opens into the fourth microfluidic duct and forms a second fluidic junction therewith; and an outlet that is in fluid communication with the second fluidic junction.

In certain embodiments, the microfluidic device comprises a first microfluidic duct for delivering a first fluid; a second microfluidic duct for delivering a second fluid, the second fluid being immiscible with the first fluid; wherein the first microfluidic duct opens into the second microfluidic duct and forms a first fluidic junction therewith; a third microfluidic duct that is in fluid communication with the first fluidic junction and is wettable by the second fluid; a fourth microfluidic duct for delivering a third fluid; wherein the third microfluidic duct opens into the fourth microfluidic duct and forms a second fluidic junction therewith, a fifth microfluidic duct that originates from the second fluidic junction and is wettable by the third fluid; a sixth microfluidic duct for delivering a fourth fluid; wherein the fifth microfluidic duct opens into the sixth microfluidic duct and forms a third fluidic junction therewith; and an outlet that is in fluid communication with the third fluidic junction.

In certain embodiments, the first fluidic junction is selected from the group consisting of a flow-focusing junction and a t-junction. In other embodiments, the second fluidic junction is a flow-focusing junction. In yet other embodiments, the third microfluidic duct is at least partially coated with a polymer that is wettable by the second fluid. In yet other embodiments, the first and second fluidic junctions are independently selected from the group consisting of a flow-focusing junction and a t-junction. In yet other embodiments, the third fluidic junction is a flow-focusing junction. In yet other embodiments, the third microfluidic duct is at least partially coated with a polymer that is wettable by the second fluid. In yet other embodiments, the fifth microfluidic duct is at least partially coated with a polymer that is wettable by the third fluid.

In certain embodiments, the method of preparing a microfiber comprises the steps of: providing a microfluidic device in accordance with the present invention; delivering a first fluid to the first microfluidic duct and a second fluid to the second microfluidic duct, whereby a first emulsion comprising the first fluid into the second fluid is formed within or in the proximity of the first fluidic junction; and delivering a third fluid to the fourth microfluidic duct, whereby a mixture of the third fluid and the first emulsion is formed within or in the proximity of the second fluidic junction; and allowing the microfiber to form within or in the proximity of the outlet of the second fluidic junction.

In certain embodiments, the method of preparing a microfiber comprises the steps of: providing a microfluidic device in accordance with the present invention; delivering a first fluid to the first microfluidic duct and a second fluid to the second microfluidic duct, whereby a first emulsion comprising the first fluid within the second fluid is formed within or in the proximity of the first fluidic junction; delivering a third fluid to the fourth microfluidic duct, whereby a second emulsion comprising the first emulsion within the third fluid is formed within or in the proximity of the second fluidic junction; delivering a fourth fluid to the sixth microfluidic duct, whereby a mixture of the fourth fluid and the second emulsion is formed; and allowing the microfiber to form within or in the proximity of the outlet of the third fluidic junction.

In certain embodiments, the system comprises a microfluidic device and first, second and third fluid reservoirs; wherein the microfluidic device comprises first, second, third and fourth microfluidic ducts and an outlet; wherein the first fluid reservoir comprises a first fluid and is in fluid communication with the first microfluidic duct; wherein the second fluid reservoir comprises a second fluid and is in fluid communication with the second microfluidic duct, the second fluid being immiscible with the first fluid; wherein the first microfluidic duct opens into the second microfluidic duct and forms a first fluidic junction therewith; wherein the third microfluidic duct is in fluid communication with the first fluidic junction and is wettable by the second fluid; wherein the third fluid reservoir comprises a third fluid and is in fluid communication with the fourth microfluidic duct; wherein the third microfluidic duct opens into the fourth microfluidic duct and forms a second fluidic junction therewith; and the outlet is in fluid communication with the second fluidic junction.

In certain embodiments, the system comprises a microfluidic device and first, second, third and fourth fluid reservoirs, wherein the microfluidic devices comprises first, second, third, fourth, fifth and sixth microfluidic ducts and an outlet, wherein the first fluid reservoir comprises a first fluid and is in fluid communication with the first microfluidic duct, wherein the second fluid reservoir comprises a second fluid and is in fluid communication with the second microfluidic duct, the second fluid being immiscible with the first fluid, wherein the first microfluidic duct opens into the second microfluidic duct and forms a first fluidic junction therewith; wherein the third microfluidic duct is in fluid communication with the first fluidic junction and is wettable by the second fluid; wherein the third fluid reservoir comprises a third fluid and is in fluid communication with the fourth microfluidic duct, wherein the third microfluidic duct opens into the fourth microfluidic duct and forms a second fluidic junction therewith; wherein the fifth microfluidic duct originates from the second fluidic junction and is wettable by the third fluid; wherein the fourth fluid reservoir comprises a fourth fluid and is in fluid communication with the sixth microfluidic duct; wherein the fifth microfluidic duct opens into the sixth microfluidic duct and forms a third fluidic junction therewith; and wherein the outlet is in fluid communication with the third fluidic junction.

In certain embodiments, the method of physically displacing a microfiber comprises applying a magnetic field to a microfiber in accordance with the present invention, wherein the microfiber comprises a magnetic compound, whereby the microfiber is physically displaced.

In certain embodiments, the microfiber comprises a matrix material; wherein the microfiber further comprises a plurality of droplets embedded in the matrix material along the length thereof; wherein each one of the plurality of droplets independently comprises a single fluid; wherein the matrix material of the microfiber is insoluble in each one of the plurality of droplets; and wherein at least one selected from the group consisting of the matrix material and at least one of the plurality of droplets comprises a magnetic compound.

In certain embodiments, the microfiber comprises a matrix material; wherein the microfiber further comprises a plurality of droplets embedded in the matrix material along the length thereof; wherein each one of the plurality of droplets independently comprises an emulsion comprising a first droplet phase within a second droplet phase; wherein the matrix material of the microfiber is insoluble in the second droplet phase of each one of the plurality of droplets; and wherein at least one selected from the group consisting of the matrix material and at least one of the plurality of droplets comprises a magnetic compound.

In certain embodiments, the microfiber comprises an outer matrix material and an inner matrix material, wherein the outer matrix material and the inner matrix material span the length of the microfiber; wherein the inner matrix material is embedded in the outer matrix material; wherein the microfiber further comprises a plurality of droplets embedded in the inner matrix material along the length thereof; wherein the inner matrix material of the microfiber is insoluble in each one of the plurality of droplets and in the outer matrix material; and wherein at least one selected from the group consisting of the matrix material and at least one of the plurality of droplets comprises a magnetic compound.

BRIEF DESCRIPTION OF THE FIGURES

For the purpose of illustrating the invention, there are depicted in the drawings certain embodiments in accordance with the present invention. However, the invention is not limited to the precise arrangements and instrumentalities of the embodiments depicted in the drawings.

DETAILED DESCRIPTION OF THE INVENTION

Figure 1:
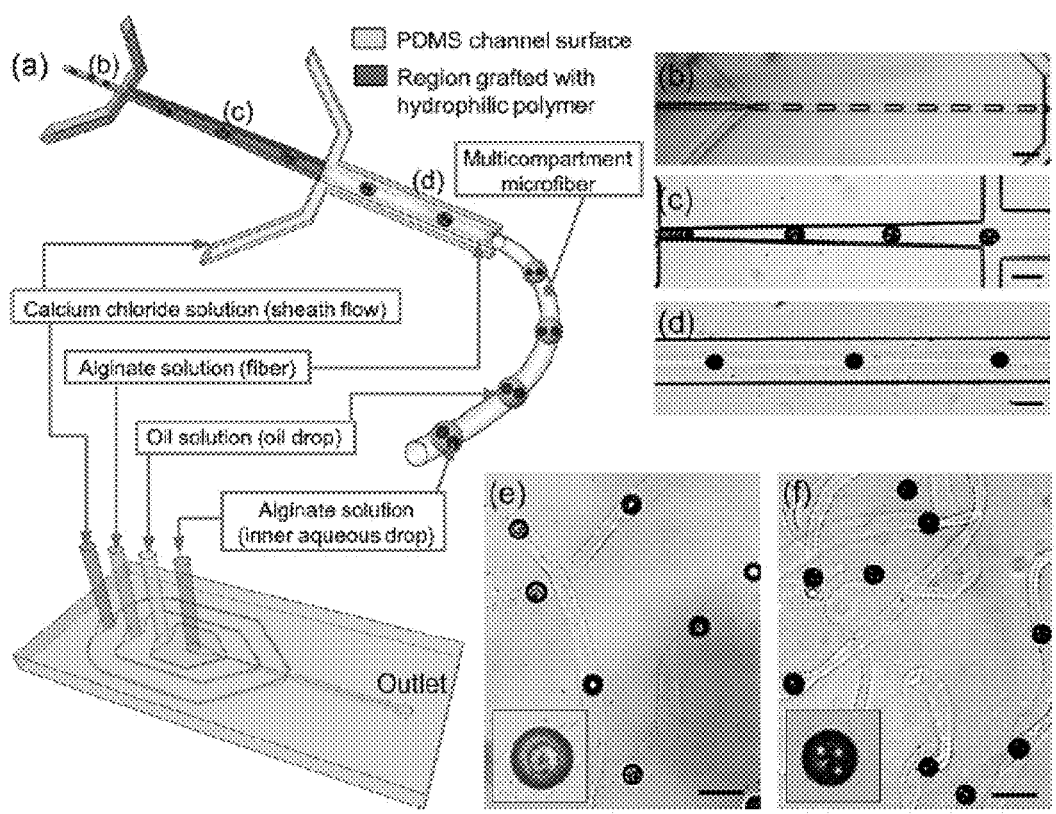
FIG. 1 is a non-limiting illustration of microfluidic devices and compositions in accordance with the present invention. Panel (a) illustrates a non-limiting microfluidic device geometry designed for generating alginate particle-in-oil compartments encapsulated in an alginate fiber. The enlarged part of the channel shows each step of the in situ fabrication of the multicompartment fibers, with the hydrophilic region of the channel indicated in dark grey (red). All the inlets for each solution used in generating multicompartment fibers are indicated in the schematic device. Panels (b)-(d) illustrate microscope images showing each step of the multicompartment fiber fabrication including: panel (b)—inner alginate particle generation in an oil phase; panel (c)—alginate-in-oil double emulsion formation in the region grafted with hydrophilic polymer; panel (d)—formation of the complete composite alginate fiber containing double emulsion droplets and sheathed by an aqueous solution of calcium chloride in the main channel. Panels (e)-(f) illustrate resulting fibers collected from the outlet containing double emulsions that consist of (panel (e)) a single alginate particle per oil compartment, and (panel (f)) multiple alginate particles per oil compartment. Scale bars=200 µm.

The present invention provides novel methods and devices for preparing multi-compartment microfibers comprising droplets embedded along the length of the fiber. The present invention further provides microfibers prepared using the methods and/or devices recited herein. Fibers in accordance with the present invention can be used, for example, for the efficient storage and release of multiple cargos. Such fibers can also, for example, comprise magnetic materials, allowing for external actuation.

In certain embodiments, the present invention provides a passive microfluidic process that comprises a droplet generation step and a fiber formation step. In other embodiments, the inventive microfluidic methods and devices allow for the in situ fabrication of novel composite fibers based on the droplet-in-fiber structure.

The present disclosure recites a passive microfluidic approach to the fabrication of multicompartment fibers that exhibit a droplet-in-fiber structure. The inventive methods and devices allow for embedding double emulsion droplets in fibers, which may be hydrophobic or hydrophilic, (comprising, in a non-limiting example, alginate and polyethylene glycol di-acrylate (PEG-DA), and allow for encapsulation of various materials, both hydrophilic/hydrophobic, solid/liquid, and biological/inorganic. For example, the inventive methods and devices allow for preparing encapsulating fibers with a magnetic property, or for preparing a cell scaffold, so that cell behaviors in response to certain chemicals compartmentalized within the fiber can be studied.

The hierarchical structure of the inventive fibers allows for more choices on the materials to be encapsulated in the fiber itself, and on the solvents used to release the material. Unlike a method that employs solvent evaporation of the oil droplets for incorporating polymer spheres in a fiber, the inventive methods allow for encapsulating double emulsions inside the fiber, and for creating hydrogel particles inside the fiber. These embedded double emulsion droplets arranged along the length of the fiber provide a heterogeneous microenvironment where distinct microcompartments have alternating hydrophilic or hydrophobic characteristics, as well as contrasting physical states (for example, solid versus liquid).

The alternating properties of the microcompartments, where there are repeating regions with alternating hydrogel-oil-hydrogel environments, can be used for the co-encapsulation of both lipophilic and hydrophilic compounds. Such fiber structures can be used, for example, for the co-encapsulation and co-delivery of compounds with incompatible solubilities, selective dissolution, and multifunctionality.

In certain embodiments, the microfluidic methods of the present invention are modular, and the devices of the present invention comprise distinct regions for sequential generation of each of the components that makes up the final fiber structure. This modular approach makes it possible to add various droplet operations, such as alternating droplet flow for introducing distinct chemistries, or modules to control the length and shape of the fibers, which can be used to generate more advanced fiber structures with greater composition and geometry control for diverse applications.

It is difficult to stably deliver drugs to the specific site using microcapsules or microparticles, because those usually show high initial burst release rates. In contrast, the core-droplet generation in the fiber is a robust method of compartmentalization at the microscale. Further, the droplets-in-fiber of the present invention enables more spatiotemporal control in the release profile, and also allows for either simultaneous or sequential delivery of multiple materials. The compartmentalization within the fibers of the present invention allow for compounds not commonly combined within one construct, possibly due to incompatible solubilities or the need for very different release profiles, to be combined within the same structure, stored within their preferred microenvironment, and co-delivered to the desired target.

In certain embodiments, the methods of the present invention allow for the fabrication of composite fiber structures that exhibit a high level of spatial control within the fiber structure. In other embodiments, the methods of the present invention allow for embedding droplets at regularly spaced positions along the length of the fiber. In yet other embodiments, the methods of the present invention allow for embedding droplets at preselected positions, within experimental error, along the length of the fiber.

In certain embodiments, the droplets-in-fiber structure is a one-dimensional array of stored droplets, and thus temporal order of droplet production is preserved within the fiber structure. When generating only droplets or particles via a sequential process such as a microfluidic process, the information of each particle, such as temporal order of production and the sequence of multiple and varying chemistries, is lost when collected in the outlet. Current technology needs a method to incorporate an index in each particle to save the information. The present invention saves the spatiotemporal information of droplet generation by keeping the droplets in order inside the fiber as they are produced.

In certain embodiments, the present invention has an advantage over typical methods of dispersing functional microparticles in polymer because it produces ordered composites as opposed to a random dispersion of the particles in bulk polymer. The in situ production of droplets-in-fiber controls the dispersity of the particles and the spatial alignment of different materials.

The encapsulation capabilities of the fiber structures of the present invention were demonstrated by testing the ease of loading various cargos within each type of microcompartment in the fiber, where the cargo can be a model drug or a component that adds functionality to the fiber, such as magnetic properties. In a non-limiting example, the fiber of the present invention can be used as a cell scaffold, allowing for loading of distinct chemicals in the droplet. In certain embodiments, cells can be easily encapsulated in the fiber through the microchannel along with the double emulsion droplets, and the cells dispersed in the fiber can eventually grow for several days into densely packed aggregates. In another non-limiting example, the distinct microcompartments present in the fibers of the present invention, including the outer fiber body and each of the droplet compartments, can be selectively dissolved or removed by exposure to solvents of suitable polarity.

The microfibers of the present invention may be utilized in a novel delivery system for therapeutics, such as wound dressing with encapsulated functional drugs or antibiotics. Another exemplary use of the microfibers of the present invention is in tissue engineering as a tissue scaffold, where biodegradable and biocompatible compounds are used in the fiber composition. Cells can be grown within or on the composite fiber and their positions can be controlled depending on the cells' affinity for the compartments in the fiber. Furthermore, one of the compartments can be utilized to physically manipulate the fibers, such as encapsulation of magnetic particles to move the fiber under magnetic force, while other compartments retain their functionality.

DEFINITIONS

As used herein, each of the following terms has the meaning associated with it in this section.

As used herein, unless defined otherwise, all technical and scientific terms generally have the same meaning as commonly understood by one of ordinary skill in the art to which this invention belongs. Generally, the nomenclature used herein and the laboratory procedures in surface chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "fluid" refers to a homogeneous or heterogeneous phase that is capable of demonstrating fluidic (flowing) behavior under the experimental conditions under consideration. In certain embodiments, a fluid comprises a liquid or a gas. In other embodiments, the fluid consists essentially of a liquid or a gas. In yet other embodiments, the fluid consists of a liquid or a gas.

As used herein, the term "instructional material" includes a publication, a recording, a diagram, or any other medium of expression that may be used to communicate the usefulness of the compositions, devices and/or methods of the present invention. In certain embodiments, the instructional material may be part of a kit useful for generating compositions of the present invention. The instructional material of the kit may, for example, be affixed to a container that contains compositions and/or devices of the present invention or be shipped together with a container that contains compositions and/or devices of the present invention. Alternatively, the instructional material may be shipped separately from the container with the intention that the recipient uses the instructional material and compositions, methods and/or devices cooperatively. For example, the instructional material is for use of a kit; or instructions for use of the compositions, methods and/or devices of the present invention.

As used herein, the term "microdevice" refers to a device that has at least one component with at least one spatial dimension less than 1 millimeter.

As used herein, the term "µm" is the abbreviation for "micron" or "micrometer", and it is understood that 1 µm=0.001 mm=$10^{-6}$ m=1 millionth of a meter.

As used herein, the term "nanodevice" refers to a device that has at least one component with at least one spatial dimension less than 1 micron.

As used herein, the term "nm" is the abbreviation for "nanometer" and it is understood that 1 nm=1 nanometer=$10^{-9}$ m=1 billionth of a meter.

As used herein, the term "soluble" as applied to two or more phases refers to the fact that the two or more phases can mix and stay as a resulting homogenous phase without significant phase separation over time. In a non-limiting example, water and hydrophobic liquids (such as oils and liquid waxes) are not substantially soluble in each other.

As used herein, the term "tween 80" refers to a polyethylene sorbitol ester also known as Polysorbate 80, PEG (80) sorbitan monooleate, or polyoxyethylenesorbitan monooleate.

As used herein, the term "wettable by a fluid" as applied to a material refers to the fact that the material has similar polarity, chemical composition and/or physical composition to the fluid and the material have favorable molecular interactions. In certain embodiments, a hydrophilic fluid has a lower contact angle than a hydrophobic fluid when interacting with a hydrophilic material. In other embodiments, a hydrophobic fluid has a lower contact angle than a hydrophilic fluid when interacting with a hydrophobic material. In yet other embodiments, a hydrophilic fluid has a higher spreading coefficient than a hydrophobic fluid when interacting with a hydrophilic material. In other embodiments, a hydrophobic fluid has a higher spreading coefficient than a hydrophilic fluid when interacting with a hydrophobic material.

Throughout this disclosure, various aspects of the present invention may be presented in a range format. It should be understood that the description in range format is merely for convenience and brevity and should not be construed as an inflexible limitation on the scope of the present invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6, and so on, as well as individual numbers within that range, for example, 1, 2, 2.7, 3, 4, 5, 5.3, and 6. This applies regardless of the breadth of the range.

Disclosure

Figure 11:
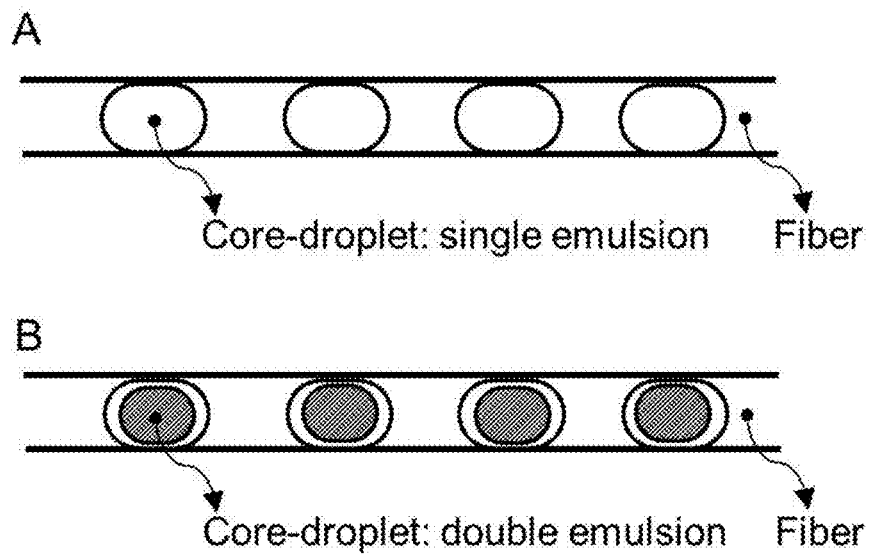
FIG. 11 is a non-limiting diagrammatic illustration of an exemplary composition of droplets-in-fiber with core droplets in the form of (panel A) single emulsions and (panel B) double emulsions.

In certain embodiments, the methods and devices of the present invention allow for the preparation of a fiber comprising core-droplets arranged along the length of the fiber at regularly spaced and/or specific locations. The core-droplets can be either single emulsions (FIG. 11, panel A) or multiple emulsions, such as double emulsions (FIG. 11, panel B).

A wide range of materials, which are in liquid state prior to solidification, can be used to prepare the fibers of the present invention. For example, fibers can be synthesized from precursor solutions using polymerization (for example, photochemical polymerization or thermal polymerization), solvent extraction (or phase inversion), covalent crosslinking (for example, covalently crosslinking a protein or any other amine-containing polymer with glutaraldehyde or any other oligo- or polyaldehyde) and/or ionic crosslinking (for example, alginate and a polyvalent ion such as $Ca^{2+}$). For example, biodegradable hydrophobic polyester fibers can be synthesized from polymer solutions using solvent extraction to achieve solidification.

The composition of the core-droplets, which is immiscible with the continuous phase in which it forms, can also be widely varying. In certain embodiments, a drops-in-fiber configuration has adjacent phases in the fiber structure alternating with respect to their hydrophobic/hydrophilic properties. In other embodiments, in the case of drops-in-fiber structures generated from aqueous two phase systems (ATPS), all compartments in the fiber may be hydrophilic. Each of the phases—the outer fiber body and each of the layers in the core-droplets—may also contain materials that are dissolved or dispersed in the precursor solutions prior to fiber generation and become encapsulated within that phase of the fiber.

In certain embodiments, the core droplets are solid, thus ensuring that the droplets do not escape the fiber body. Such embodiments may be beneficial, for example, when the inner water droplets in water-in-oil-in-alginate fibers are unstable and tend to escape the middle oil phase to merge with the outer fiber phase. The core droplets may be solidified using polymerizable materials, such as alginate and others. Alternatively, liquid core droplets may be stabilized with various surfactant and nanoparticle stabilizers, such as in Pickering emulsions.

In certain embodiments, the process of generating droplets-in-fiber structures uses passive microfluidic devices that rely on droplet breakup and hydrodynamic focusing mechanisms. One such device comprises, for example, a sequence of modular device operations, such as a flow-focusing junction or t-junction, where each module adds to the complexity of the fiber structure and composition. This modular approach makes it possible to add distinct droplet operations, such as alternating droplet flow for alternating chemistries, into the overall device geometry for added complexity in the fiber structure. The specific methods for producing single emulsion and double emulsion droplets-in-fiber structures are illustrated herein in non-limiting embodiments.

In non-limiting embodiments, the method of generating droplets-in-fiber (single emulsion) includes the following steps. Step 1: generation of core-droplets in continuous phase 1. Step 2: fiber formation from continuous phase 1 in continuous phase 2.

Continuous phase 1 templates the final solid fiber structure. Continuous phase 2 is a sheath flow that focuses the stream of continuous phase 1, and may contain chemicals that trigger solidification of the stream of continuous phase 1. The composition of the solution of the core-droplets is selected so that it is immiscible with continuous phase 1, allowing for the formation of droplets. In non-limiting examples, the core-droplets are oil immiscible with an aqueous alginate solution of continuous phase 1, and continuous phase 2 is an aqueous stream with dissolved calcium chloride. In that particular case, the calcium ions crosslink the alginate stream to form the fiber with encapsulated oil droplets. Alternatively, in non-limiting examples, the core-droplets are oil immiscible with an aqueous polyamine solution of continuous phase 1, and continuous phase 2 is an aqueous stream with dissolved glutaraldehyde or another polyaldehyde; or the core-droplets are oil immiscible with an aqueous acrylamide/bisacrylamide solution of continuous phase 1, and continuous phase 2 is an aqueous stream with dissolved ammonium persulfate or another soluble oxidant, and so on.

Figure 12:
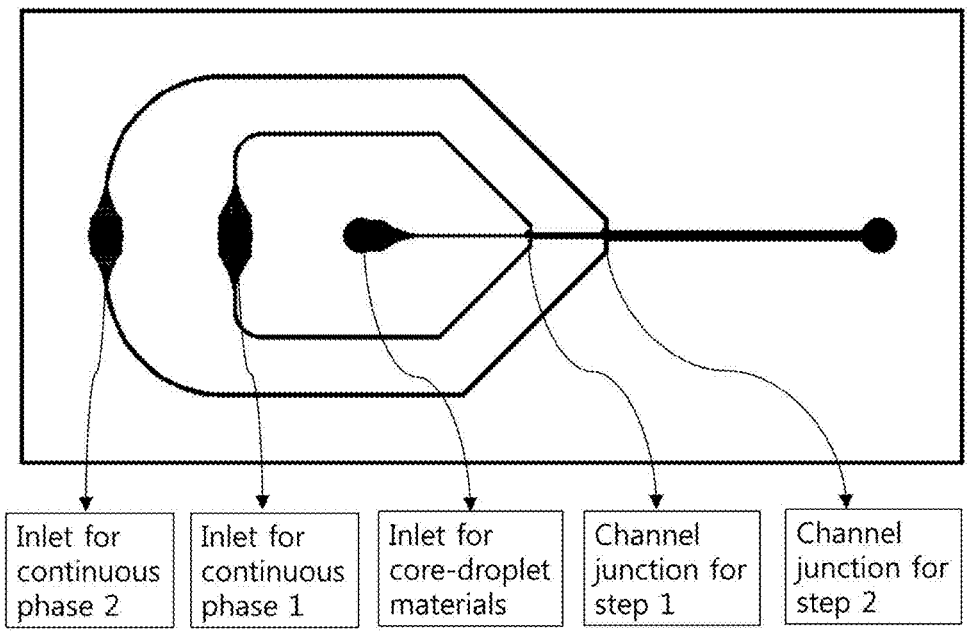
FIG. 12 is a non-limiting diagrammatic illustration of an exemplary microfluidic device for making droplets-in-fiber (single emulsion).

In certain embodiments, the device for making droplets-in-fiber (single emulsion) includes modules for generating core-droplets in continuous phase 1, and forming fibers from continuous phase 1 in continuous phase 2. For step 1, the channel module can be in the form of a focusing channel or t-junction. For step 2, the channel module can be in the form of a focusing channel (FIG. 12)

In non-limiting embodiments, the method for generating droplets-in-fiber (double emulsion) includes the following steps. Step 1: generation of core-droplets in continuous phase 1. Step 2: generation of double-emulsions (core-droplets in continuous phase 1) in continuous phase 2. Step 3: fiber formation from continuous phase 2 in continuous phase 3.

Continuous phase 1 is the outer layer of the double emulsion droplets. Continuous phase 2 becomes the outer fiber structure. Continuous phase 3 is a sheath flow which focuses the stream of continuous phase 2 to form the fiber, and may contain chemicals that trigger solidification of the fiber. In certain embodiments, the core-droplets comprise an alginate solution, and continuous phase 1 comprises an oil phase immiscible with the alginate solution. In other embodiments, continuous phase 2 comprises an alginate solution, and continuous phase 3 comprises calcium chloride solution; or continuous phase 2 comprises a polyamine solution, and continuous phase 3 comprises a solution comprising glutaraldehyde or another polyaldehyde; or continuous phase 2 comprises an aqueous acrylamide/bisacrylamide solution, and continuous phase 3 comprises ammonium persulfate or another aqueous oxidant.

Figure 13:
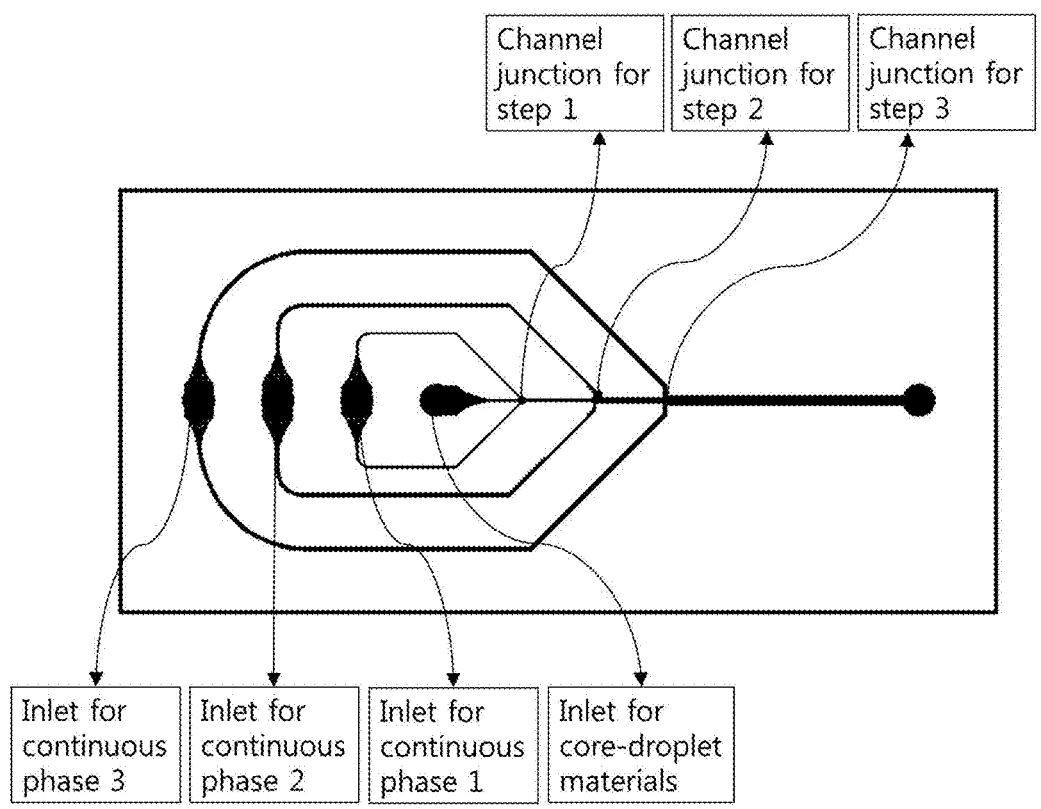
FIG. 13 is a non-limiting diagrammatic illustration of an exemplary microfluidic device for making droplets-in-fiber (double emulsion).

In certain embodiments, the device for making droplets-in-fiber (double-emulsion) comprises modules for generating core-droplets in continuous phase 1, generating double emulsions (core-droplets in continuous phase 1) in continuous phase 2, and forming fibers from continuous phase 2 in continuous phase 3. For step 1 and step 2, the channel module can be in the form of a focusing channel or t-junction. For step 3, the channel module can be in the form of a focusing channel (FIG. 13)

Microfluidic devices can be fabricated from any material that can form a channel structure, such as polydimethylsiloxane (PDMS), glass, silicon, polycarbonate, thiolene based resins (Norland Optical Adhesive), and/or polymethylmethacrylate. The mold of the microchannel can be fabricated using, for example, a conventional photolithography technique, etching, milling, 3D printing, and pulled glass capillaries. The channel structures can be bonded to form a closed channel with openings for inlets and outlets.

Figure 14:
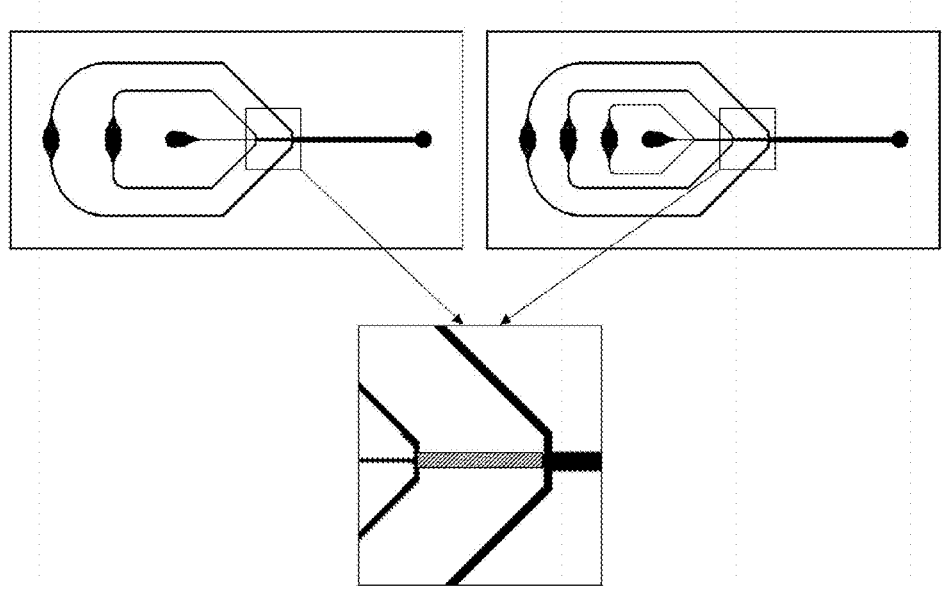
FIG. 14 is a non-limiting diagrammatic illustration of selective grafting of the channel region (hatched) with hydrophilic polymer for robust oil droplet generation in a hydrophobic channel.
Figure 15:
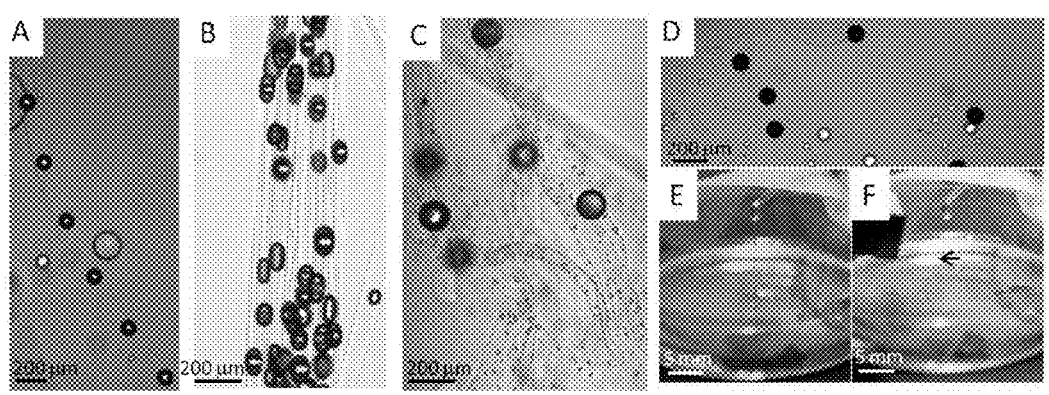
FIG. 15 is a set of non-limiting examples of drops-in-fiber structures generated using a microfluidic method in accordance with the present invention: (panel A) mineral oil-in-alginate microfibers, (panel B) aligned alginate-in-mineral oil-in-alginate microfibers, where the core alginate regions contained polystyrene nanoparticles, (panel C) alginate-in-mineral oil-in-alginate microfibers, where the outer alginate fiber contained fibroblast cells, and (panel D) alginate-in-ferrofluid-in-alginate microfiber. As illustrated in panel E, the fiber fell vertically when collected but, as illustrated in panel F, the fiber was deflected in the presence of a magnet.

In certain embodiments, the surface wetting characteristics of the microchannel walls are of interest when forming multiple emulsions. In other embodiments, the continuous phase has to appropriately wet the walls in the region of the microchannel, so that stable droplets of the non-wetting phase are formed therein. For example, in order to generate aqueous phase core-droplets in a continuous oil phase, the channel walls should be hydrophobic. For the inverse emulsion, oil/hydrophobic droplets in an aqueous stream, the channel walls must be hydrophilic. To vary the wetting properties of the channel walls, graft hydrophilic polymer can be selectively grafted in desired regions of a hydrophobic channel. In non-limiting examples, in a hydrophobic microfluidic channel the region of oil droplet generation in aqueous phase is selectively grafted with hydrophilic polymer for example, poly(acrylic acid) (FIG. 14). Other methods can be used to selectively functionalize PDMS, for example, layer-by-layer deposition of polyelectrolytes (Bauer, et al., 2010 Lab Chip 10:1814) and photoreactive sol-gel coatings (Abate, et al., 2008 Lab Chip 8:2157).

Compositions

The invention provides microfibers, which are exemplified in a non-limiting manner herein. The invention should not be construed to be limited to the description herein, and contemplates any combination(s) of the embodiments recited herein.

In one aspect, the invention provides a microfiber comprising a matrix material, wherein the microfiber further comprises a plurality of droplets embedded in the matrix material along the length thereof. Each one of the plurality of droplets independently comprises a single fluid, and is insoluble in the matrix material of the microfiber.

In another aspect, the invention provides a microfiber comprising a matrix material, wherein the microfiber further comprises a plurality of droplets embedded in the matrix material along the length thereof. Each one of the plurality of droplets independently comprises an emulsion comprising a first droplet phase within a second droplet phase. Further, the matrix material of the microfiber is insoluble in the second droplet phase of each one of the plurality of droplets.

In yet another aspect, the invention provides a microfiber comprising an outer matrix material and an inner matrix material; wherein the outer matrix material and the inner matrix material span the length of the microfiber; and wherein the inner matrix material is embedded in the outer matrix material. The microfiber further comprises a plurality of droplets embedded in the inner matrix material along the length thereof. Further, the inner matrix material of the microfiber is insoluble in each one of the plurality of droplets and in the outer matrix material.

In certain embodiments, the matrix material is hydrophilic. In other embodiments, the matrix material is hydrophobic.

In certain embodiments, the matrix material is prepared from a precursor using at least one method selected from the group consisting of polymerization, solvent extraction, ionic crosslinking and covalent crosslinking. In other embodiments, the matrix material is prepared from a precursor using at least one method selected from the group consisting of polymerization, solvent extraction, and covalent crosslinking. In yet other embodiments, the matrix material is not prepared from a precursor using ionic crosslinking. In yet other embodiments, the matrix material is not prepared from a precursor using polymerization. In yet other embodiments, the matrix material is not prepared from a precursor using solvent extraction. In yet other embodiments, the matrix material is not prepared from a precursor using ionic crosslinking. In yet other embodiments, the matrix material is not prepared from a precursor using covalent crosslinking.

The composition of any of the matrix materials contemplated may vary, or not vary, along the length of the microfiber. Likewise, each one of the plurality of the droplets has a like composition, or the compositions of the plurality of the droplet are not identical among themselves. The fibers may comprise at least one agent selected from the group consisting of a cell, tissue, filler, therapeutic drug, chemoattractant, biocide, ion, peptide, protein, nucleic acid, magnetic compound, and detectable probe. Such agent may be embedded in the matrix material or in at least one of the plurality of droplets. In the case that such agent is magnetic compound (such as, but not limited to, iron, nickel, cobalt, oxides thereof, and the like), the fiber can interact with magnetic fields and may be manipulated physically by exposure to a magnetic field (such as the magnetic field of a magnet).

In certain embodiments, the fluid comprising a droplet and the matrix material in which the droplet is embedded have distinct polarity and solubility profiles, so that they cannot dissolve in each other. For example, one may be hydrophobic and the other may be hydrophilic, and vice versa.

In certain embodiments, the fiber comprises an outer matrix material and an inner matrix material, both materials spanning the length of the fiber. In other embodiments, those materials may be coaxially aligned with each other. In yet other embodiments, those materials may be located so that they do not share the same longitudinal axis. In yet other embodiments, the radius of at least one selected from the group consisting of the outer matrix material and inner matrix material is substantially constant along the length of the microfiber.

In certain embodiments, the fibers have an average width selected from the group consisting of: from about 10 µm to about 1 mm, from about 10 µm to about 900 µm, from about 10 µm to about 800 µm, from about 10 µm to about 700 µm, from about 10 µm to about 600 µm, from about 10 µm to about 500 µm, from about 10 µm to about 400 µm, from about 10 µm to about 300 µm, from about 10 µm to about 200 µm, from about 10 µm to about 100 µm, from about 100 µm to about 1 mm, from about 100 µm to about 900 µm, from about 100 µm to about 800 µm, from about 100 µm to about 700 µm, from about 100 µm to about 600 µm, from about 100 µm to about 500 µm, from about 100 µm to about 400 µm, from about 100 µm to about 300 µm, from about 100 µm to about 200 µm, and any fractions or multiples thereof.

In certain embodiments, the fibers have an average length that is equal to or greater than a value selected from the group consisting of: about 100 µm, about 200 µm, about 300 µm, about 400 µm, about 500 µm, about 600 µm, about 700 µm, about 800 µm, about 900 µm, about 1 mm, about 2 mm, about 5 mm, about 10 nm, about 20 mm, about 40 mm, about 60 mm, about 80 mm, about 100 mm, about 200 mm, about 400 mm, about 600 mm, about 800 mm, about 1 m, or any fractions or multiples thereof.

In certain embodiments, the droplets embedded in the fibers have an average diameter selected from the group consisting of: about 10 µm, about 20 µm, about 30 µm, about 40 µm, about 50 µm, about 60 µm, about 70 µm, about 80 µm, about 90 µm, about 100 µm, about 200 µm, about 300 µm, about 400 µm, about 500 µm, and any fractions or multiples thereof.

In certain embodiments, the linear distance between two consecutive droplets embedded in a fiber is independently selected from the group consisting of: about 100 µm, about 200 µm, about 300 µm, about 400 µm, about 500 µm, about 600 µm, about 700 µm, about 800 µm, about 900 µm, about 1 mm, about 2 mm, about 5 mm, about 10 nm, about 20 nm, about 40 nm, about 60 nm, about 80 nm, about 100 nm, or any fractions or multiples thereof.

Devices and Systems

The present invention provides devices for preparing microfibers, which are exemplified in a non-limiting manner herein. The invention should not be construed to be limited to the description herein, and contemplates any combination(s) of the embodiments recited herein.

The present invention provides a microfluidic device such as, but not limited to, the device illustrated in FIG. 12. The device comprises a first microfluidic duct for delivering a first fluid ("core-droplet materials"); a second microfluidic duct for delivering a second fluid ("continuous phase 1"), the second fluid being immiscible with the first fluid, wherein the first microfluidic duct opens into the second microfluidic duct and forms a first fluidic junction therewith ("channel junction for step 1"). The device further comprises a third microfluidic duct that is in fluid communication with the first fluidic junction and is wettable by the second fluid; a fourth microfluidic duct for delivering a third fluid ("continuous phase 2"), wherein the third microfluidic duct opens into the fourth microfluidic duct and forms a second fluidic junction therewith ("channel junction for step 2"). The device further comprises an outlet that is in fluid communication with the second fluidic junction.

The present invention further provides a microfluidic device such as, but not limited to, the device illustrated in FIG. 13. The device comprises a first microfluidic duct for delivering a first fluid ("core-droplet materials"); a second microfluidic duct for delivering a second fluid ("continuous phase 1"), the second fluid being immiscible with the first fluid, wherein the first microfluidic duct opens into the second microfluidic duct and forms a first fluidic junction therewith ("channel junction for step 1"). The device further comprises a third microfluidic duct that is in fluid communication with the first fluidic junction and is wettable by the second fluid; a fourth microfluidic duct for delivering a third fluid ("continuous phase 2"), wherein the third microfluidic duct opens into the fourth microfluidic duct and forms a second fluidic junction therewith ("channel junction for step 2"). The device further comprises a fifth microfluidic duct that originates from the second fluidic junction and is wettable by the third fluid; a sixth microfluidic duct for delivering a fourth fluid ("continuous phase 3"), wherein the fifth microfluidic duct opens into the sixth microfluidic duct and forms a third fluidic junction therewith ("channel junction for step 3"). The device further provides an outlet that is in fluid communication with the third fluidic junction.

The present invention further provides a system comprising a microfluidic device and first, second and third fluid reservoirs. The microfluidic device comprises first, second, third and fourth microfluidic ducts and an outlet. The first fluid reservoir comprises a first fluid and is in fluid communication with the first microfluidic duct. The second fluid reservoir comprises a second fluid and is in fluid communication with the second microfluidic duct, the second fluid being immiscible with the first fluid. The first microfluidic duct opens into the second microfluidic duct and forms a first fluidic junction therewith. The third microfluidic duct is in fluid communication with the first fluidic junction and is wettable by the second fluid. The third fluid reservoir comprises a third fluid and is in fluid communication with the fourth microfluidic duct. The third microfluidic duct opens into the fourth microfluidic duct and forms a second fluidic junction therewith. The outlet is in fluid communication with the second fluidic junction.

The present invention provides a system comprising a microfluidic device and first, second, third and fourth fluid reservoirs. The microfluidic devices comprises first, second, third, fourth, fifth and sixth microfluidic ducts and an outlet. The first fluid reservoir comprises a first fluid and is in fluid communication with the first microfluidic duct. The second fluid reservoir comprises a second fluid and is in fluid communication with the second microfluidic duct, the second fluid being immiscible with the first fluid. The first microfluidic duct opens into the second microfluidic duct and forms a first fluidic junction therewith. The third microfluidic duct is in fluid communication with the first fluidic junction and is wettable by the second fluid. The third fluid reservoir comprises a third fluid and is in fluid communication with the fourth microfluidic duct. The third microfluidic duct opens into the fourth microfluidic duct and forms a second fluidic junction therewith. The fifth microfluidic duct originates from the second fluidic junction and is wettable by the third fluid. The fourth fluid reservoir comprises a fourth fluid and is in fluid communication with the sixth microfluidic duct. The fifth microfluidic duct opens into the sixth microfluidic duct and forms a third fluidic junction therewith. The outlet is in fluid communication with the third fluidic junction.

The invention contemplates any type of fluidic junction known in the art. In certain embodiments, each fluidic junction is independently selected from the group consisting of a flow-focusing junction and a t-junction. In other embodiments, at least one fluidic junction is a flow-focusing junction. In yet other embodiments, one or more additional microfluidic ducts open into one or more of the microfluidic ducts recited herein, allowing for the introduction of one or more additional fluids at any stage of preparation of the microfiber.

In certain embodiments, one or more of the microfluidic duct is at least partially coated with a polymer that is wettable by at least one of the fluids being flowed through the one or more of the microfluidic ducts, thus allowing formation of the appropriate emulsion therein.

Methods

The invention provides methods of preparing microfibers, which are exemplified in a non-limiting manner herein. The invention further provides methods of physically displacing microfibers, which are exemplified in a non-limiting manner herein. The invention should not be construed to be limited to the description herein, and contemplates any combination(s) of the embodiments recited herein.

The invention provides a method of preparing a microfiber using a device such as, but not limited to, the device illustrated in FIG. 12. According to this procedure, the first fluid ("core-droplet materials") is delivered to the first microfluidic duct and a second fluid ("continuous phase 1") is delivered to the second microfluidic duct, whereby a first emulsion comprising the first fluid into the second fluid is formed within or in the proximity of the first fluidic junction ("channel junction for step 1"). Then, a third fluid ("continuous phase 2") is delivered to the fourth microfluidic duct, whereby a mixture of the third fluid and the first emulsion is formed within or in the proximity of the second fluidic junction ("channel junction for step 1"). The microfiber is then allowed to form within or in the proximity of the outlet of the second fluidic junction.

The invention also provides a method of preparing a microfiber using a device such as, but not limited to, the device illustrated in FIG. 13. According to this procedure, the first fluid ("core-droplet materials") is delivered to the first microfluidic duct and a second fluid ("continuous phase 1") is delivered to the second microfluidic duct, whereby a first emulsion comprising the first fluid within the second fluid is formed within or in the proximity of the first fluidic junction ("channel junction for step 1"). Then, a third fluid ("continuous phase 2") is delivered to the fourth microfluidic duct, whereby a second emulsion comprising the first emulsion within the third fluid is formed within or in the proximity of the second fluidic junction ("channel junction for step 2"). Then, a fourth fluid is delivered to a sixth microfluidic duct, whereby a mixture of the fourth fluid and the second emulsion is formed ("channel junction for step 3"). The microfiber is then allowed to form within or in the proximity of the outlet of the third fluidic junction.

It should be noted that the system of the invention is modular and thus the same inlets, ducts and/or fluidic junctions need not be used throughout the preparation of the microfiber. The invention contemplates, for example, using one or more first fluids, one or more second fluids, and so forth during the preparation of a microfiber of the present invention. Further, the invention contemplates using one or more first microfluidic ducts, one or more second microfluidic ducts, and so forth during the preparation of a microfiber of the present invention. Further, the invention contemplates using one or more first fluidic junctions, one or more second fluidic junctions and so forth during the preparation of a microfiber of the present invention. Such changes in inlets, ducts and/or junctions may take place at any time during the preparation of the microfiber; they may take place by physically replacing any one of the inlets, ducts and/or fluidic junctions with another one, or by directing the microfiber-in-preparation to a new set of inlets, ducts and/or fluidic junctions by virtue of a physical barrier or a physical connection.

The invention further provides a method of physically displacing a microfiber. The method comprises applying a magnetic field to an inventive microfiber that comprises a magnetic compound. In certain embodiments, the microfiber is repelled by the magnetic field. In other embodiments, the microfiber is attracted by the magnetic field.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. Although the description herein contains many embodiments, these should not be construed as limiting the scope of the present invention but as merely providing illustrations of some of the presently preferred embodiments of the present invention.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application. In general the terms and phrases used herein have their art-recognized meaning, which can be found by reference to standard texts, journal references and contexts known to those skilled in the art. Any preceding definitions are provided to clarify their specific use in the context of the present invention.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Figure 7:
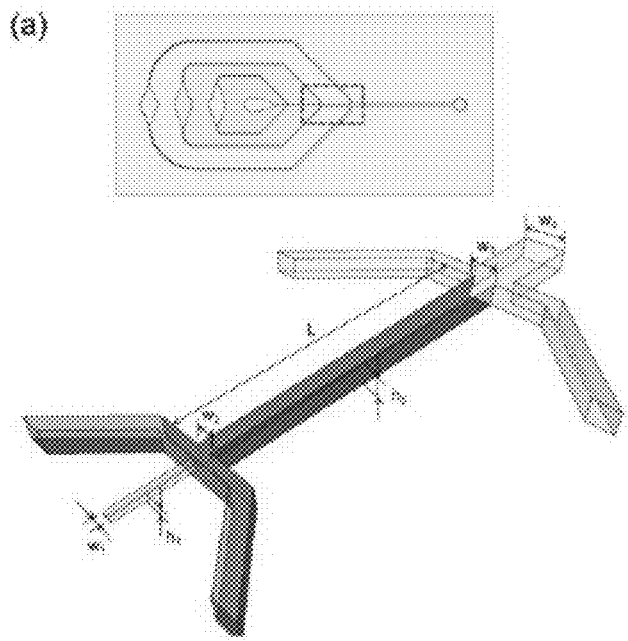
FIG. 7 illustrates non-limiting examples of exemplary microfluidic devices. Panel (a) illustrates the channel geometry of two different dimensions to fabricate the multicompartment fibers, Design 1 and Design 2. Panels (b)-(e) illustrate dimensions of the multicompartment fibers as a function of the oil phase flow rate are shown, while the flow rates of calcium chloride solution and the alginate solution for fibers were fixed to be 6 mL·hr$^{-1}$ and 0.6 mL·hr$^{-1}$, respectively. The overall distance between oil droplets in the fiber in Design 1 (panel (b)) was shorter than in Design 2 (panel (c)). The diameter of oil droplets and the width of alginate stream in Design 1 (panel (d)) and Design 2 (panel (e)) are also shown. Overall, the increase in the widths w1 and w2 (Design 2) compared to the Design 1 resulted in the larger diameters of oil droplets and the longer distance between the droplet compartments in the fiber.
Figure 7:
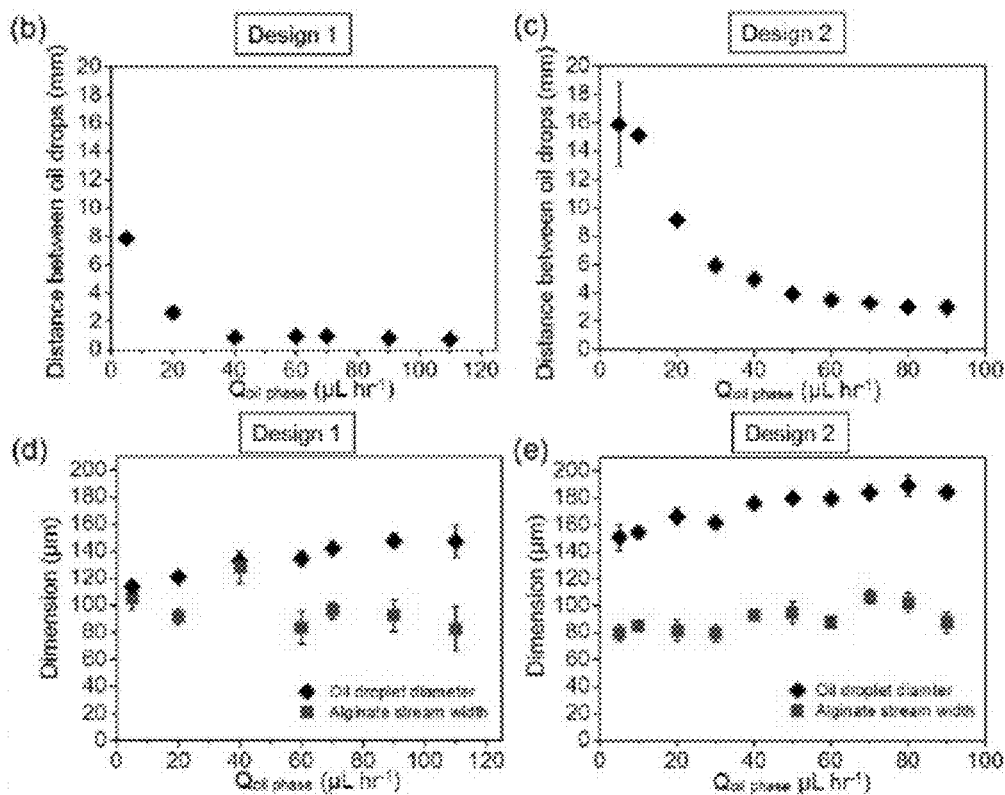

Channel Fabrication:

The microfluidic device for making multicompartment microfibers was fabricated from polydimethylsiloxane (PDMS) by soft lithography. The mold of the microchannel, including a sequence of flow-focusing channels, was fabricated by standard photolithography from photoresist (SU-8 2010 and SU-8 2025, MicroChem) on a silicon wafer. The mold of the top layer of the channel was fabricated on the silicon wafer using two-step lithography of 30 µm and 90 µm in height, and the bottom layer was fabricated to be 80 µm in height. Channel dimensions are shown in FIG. 7.

A degassed 10:1 mixture of PDMS prepolymer and curing agent (Sylgard 184, Dow Corning) was poured on the channel mold and released after 2 hours of curing at 65° C. The closed channel structure with openings for inlets and outlets was formed by bonding top and bottom layers of PDMS with plasma treatment. The devices were heated at 95° C. for a day to recover hydrophobicity of the PDMS channels, and stored in vacuum overnight, before localized grafting of the hydrophilic polymer, poly(acrylic acid) (PAA). (Schneider, et al., 2011, Langmuir 27:1232). The channel was masked with black electrical tape leaving only the region for oil droplet generation transparent. The channel was filled with 10% w/v benzophenone (photoinitiator) in acetone for 70-90 seconds, and flushed with air. Then the channel was filled with 10 wt % acrylic acid in DI water and exposed under a 335 nm-610 nm Bandpass color filter to UV light for 90-150 seconds. In this time range, the time of treatment with benzophenone and acrylic acid was increased if the oil solution wet the PAA grafted region when forming a droplet, and decreased if the alginate stream started to adhere to the channel wall upon contact with calcium chloride solution. The channel was washed with ethanol, pH 10 water, and DI water respectively, before fiber fabrication.

Chemical Sample Preparation:

For the sheath flow of the fiber formation, 1.5-2% (w/v) of calcium chloride solution in DI water was used.

For the alginate fiber, 0.5-1 wt % sodium alginate (from brown algae) with 0.1-0.25 wt % poly(vinyl alcohol) (PVA; Molecular weight, 31,000-50,000) dissolved in DI water or PBS was used. PVA is a biocompatible polymer. Also, after collecting the fibers, they were rinsed with DI water or PBS, and stored in DI water to allow any water-soluble components in the fiber to be removed. Then UV-Vis spectroscopy was used to determine the presence of PVA, which shows a maximum absorbance around 216 nm. No absorbance peaks were observed in the wavelength range 210-240 nm from the sample solution over 24 hours. For cell encapsulation, the alginate-PVA solution was filtered through 0.22 μm pore-sized filter prior to mixing with cells. The mammalian cells, NIH/3T3 mouse fibroblast cells (ATCC), were cultured in Dulbecco's modified Eagle medium (DMEM; ATCC) supplemented with 10% (v/v) calf bovine serum and 1% (v/v) penicillin. The cells were prepared to be $1\text{-}2\times10^5$ cells·mL$^{-1}$ in the final alginate solution. For encapsulating mammalian cells in the alginate fiber, a solution of 0.5 wt % alginate with 0.1 wt % PVA dissolved in PBS was used. The bacterial cells were *Escherichia coli* (*E. Coli*, S17-1λpir) that express green fluorescent protein (GFP) from a plasmid, induced by isopropyl β-D-1-thiogalactopyranoside (IPTG). More details on the cells, including plasmid construction, is recited in Drescher, et al., 2014, Curr. Biol. 24:50. The *E. coli* cells were prepared in the alginate solution to be $4\text{-}5\times10^6$ cells·mL$^{-1}$. For encapsulating bacterial cells, a solution of 1 wt % alginate with 0.25 wt % PVA dissolved in PBS was used.

For the oil droplet compartment, mineral oil with 2 wt % Span 80 was used in general. For solidifying inner alginate droplets to prevent them from escaping the oil compartment, 5% (v/v) of calcium chloride-saturated undecanol was mixed with the oil solution. The concentrations of the cargos to be carried in the oil compartment were 0.3 mg·mL$^{-1}$ for Nile red, 0.8% (v/v) for magnetic particles in oil-phase (EMG 909, FerroTec), and 10 and 20% (v/v) for eugenol. To demonstrate the antibacterial effect of the oil compartment to the bacterial cells encapsulated in the fiber, eugenol was first mixed with undecanol and added to the final concentration of 10 and 20% (v/v) in the oil compartment of 2 wt % Span 80 in mineral oil. The final concentration of undecanol in the oil solution was 5% (v/v). In the case of using just eugenol for the oil compartment, 2 wt % Span 80 was added to eugenol to form stable droplets.

The concentration of alginate-PVA solution in the inner alginate compartment was kept the same as the alginate fiber. As for the cargos, 0.5% (v/v) 200 nm orange fluorescent particles (FluoSpheres, Invitrogen), 1% (w/v) FITC conjugated BSA, or 0.04% (v/v) of 190 nm Dragon Green fluorescent particles (Uniform Dyed Microspheres, Bangs Laboratories, Inc.) were mixed with the alginate solution. For water-based magnetic particles, 2% (v/v) of 1 μm-magnetic polystyrene particles were mixed in the alginate solution. Chemicals not indicated with vendors were purchased from Sigma-Aldrich.

Fiber Collection and Treatment:

Multicompartment fibers were collected as suspensions in DI water or wound between two rotating needles controlled by a motor (Barnant Motor Mixer, Model No. 700-5412). Fibers encapsulating the fibroblast cells were collected in DMEM supplemented with 10% calf bovine serum and 1% penicillin, and stored in the 5% $CO_2$-humidified incubator at 37° C. To test the cell viability inside the multicompartment fibers, 2 μM of calcein AM and 4 μM of ethidium-homodimer-1 (EthD-1) from LIVE/DEAD Viability/Cytotoxicity kit for mammalian cells (Molecular Probes) were applied in the DMEM 1 hour prior to the observation under a fluorescent microscope. The cell viability was analyzed with the green (calcein AM) and red (EthD-1) fluorescence images using image analysis software, ImageJ (NIH). *E. coli*-encapsulated fibers were either collected in LB media containing 1 mM IPTG and 100 μg·mL$^{-1}$ Kanamycin (kanamycin sulfate; Fisher). For selective dissolution of the cargos from the oil compartment of the fibers, ethanol (Reagent alcohol, BDH) was added to the fiber suspensions. The de-crosslinking agent, 160 mM sodium citrate ($Na_3C_6H_5O_7$, Sigma-Aldrich) in DI water was used as calcium chelator to degrade the alginate fiber or inner alginate particles.

Example 1

For the work described herein, the base composition of the fiber was exemplified with calcium alginate, but the microfluidic method of the present invention can be adapted to other solidification methods such as photochemistry and solvent extraction. Alginate is a biopolymer that can undergo a mild but rapid gelation in the presence of divalent cations to form a hydrogel. Thus, the fundamental structure of the fiber consisted of an alginate-in-oil-in-alginate configuration.

Figures 5, 6:
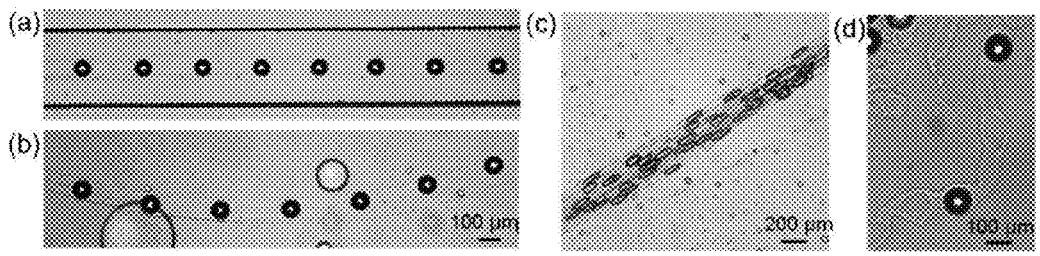
FIG. 5 illustrates bright-field images of exemplary oil droplets-in-fiber structure (panel (a)) generated inside a main channel, (panel (b)) freely suspended in an aqueous solution, and (panel (c)) spun using a motor. The fibers were stretched and therefore the shapes of inner oil compartments were elongated as well. Panel (d) illustrates resulting fibers after some of the oil droplets had escaped.
FIG. 6 is a table illustrating exemplary flow rate conditions of the inner alginate solution and the number of the inner alginate particles per oil drop at each flow rate of the oil phase. The flow rates of calcium chloride solution and the alginate solution for fibers were kept at 6 mL·hr$^{-1}$ and 0.6 mL·hr$^{-1}$, respectively.

A schematic of the channel configuration and the multicompartment fiber is illustrated in FIG. 1, panel a. Oil droplets were encapsulated in the fiber (FIG. 5), or water-in-oil double emulsion droplets were encapsulated in the fiber (FIG. 1). The hydrophobic walls of the polydimethylsiloxane (PDMS) microchannel allow for making aqueous droplets in the oil continuous phase and prevent adhesion during the production of the hydrogel fibers. In order to make oil droplets in an aqueous stream, the PDMS walls were chemically modified to become hydrophilic in that region of the microchannel. To achieve the hierarchical structuring, the microfluidic device comprises a sequence of flow-focusing junctions. At the first junction, droplets of alginate solution are generated in the oil phase, and the alginate droplets are gelled by the calcium ions in the oil phase (FIG. 1, panel b). In certain embodiments, the inner aqueous phase may be gelled because the alginate particles are more stable than aqueous droplets in the final fiber structure. At the second junction, oil droplets containing alginate particles are formed in alginate solution (FIG. 1, panel c). At the third junction, the alginate fiber with embedded alginate particle-in-oil droplets is formed as the alginate stream is focused by an outermost aqueous sheath solution containing calcium ions, which triggers solidification of the alginate stream (FIG. 1, panel d).

One advantage of using microfluidics for droplet generation is the ease of customization of the size and density of the droplet and particle microcompartments within the fiber structure. Selected studies on the dimension and the stability of droplets in the fibers are summarized in FIGS. 6-7. The methods of the present invention allow for preparation of fibers with one alginate particle per oil droplet (FIG. 1, panel e) or multiple alginate particles per oil droplet (FIG. 1, panel f) according to the flow rates described in FIG. 6. Without wishing to be limited by any theory, the flow rate of the oil phase contributes to the stability of the fiber because, at high flow rates, the oil solution may wet the channel wall. In certain embodiments, the ratio of the flow rates of the inner alginate phase to the oil phase were set at less than 0.4, so that the inner alginate phase formed stable droplets inside the oil phase. Also, the distance between the oil droplet compartments in the fiber can be controlled by the dimension of the channel and the flow rates (FIG. 7). Overall, the distance between the droplets is inversely proportional to the droplet generation frequency, which can increase with the flow rate of the oil phase and decrease with an increase in channel dimension (by producing larger volumes of the droplets). In the presently exemplified work, the distance between the droplet compartments ranged from 750 μm to 16 mm, while the diameters of the droplet compartments ranged from 113 μm to 187 The width of the alginate stream ranged from 80 µm to 128 where there were no droplets. The region surrounding the droplets were 10-20 µm thicker. The uniformity of the fiber width can be improved, for example, by incorporating oil droplets with smaller diameters compared to the width of the fiber, and also by increasing the strength of the fiber using a higher concentration of alginate in the solution.

TABLE 1

Summary of multicompartment fiber encapsulation.

| Fiber compartment | Cargo | FIG. (panel) |
|---|---|---|
| Inner alginate particle | Fluorescent nanoparticles | 2 (a); 8 (a); 4 (c) |
| | FITC-conjugated BSA | 8 (b) |
| | Magnetic microparticles | 2 (b) |
| Middle oil droplet | Fluorescent dye (Nile red) | 4 (c); 10 (a) & (c) |
| | Ferrofluid | 2 (c); 8 (c)-(f) |
| | Eugenol (antimicrobial) | 3; 10 (b) |
| Alginate fiber | NIH/3T3 fibroblast cells | 2 (c); 8 (e)-(f) |
| | Escherichia coli | 2 (d); 3; 9 |

Example 2

Figure 2:
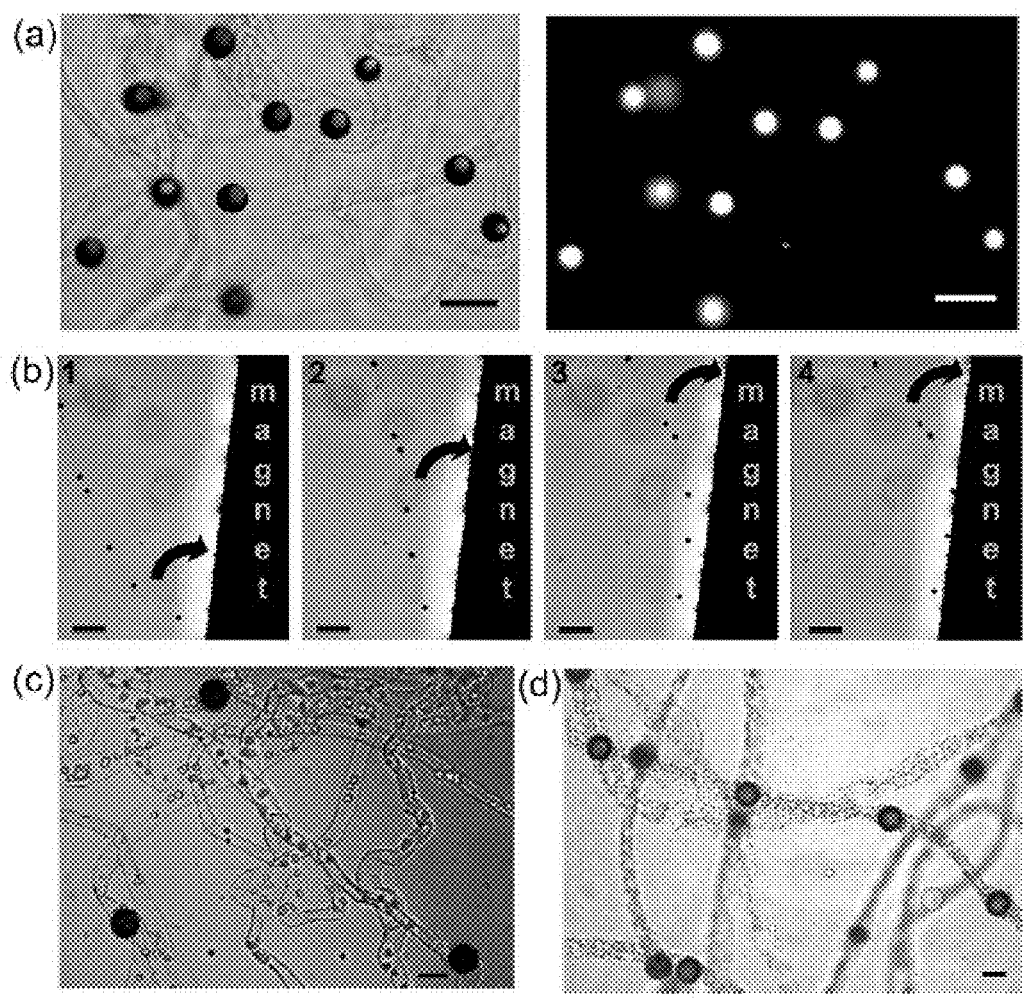
FIG. 2 illustrates non-limiting examples of encapsulation in the multicompartment fibers. Panel (a) illustrates bright-field and fluorescence images of alginate-in-oil-in-alginate fibers where fluorescent nanoparticles are encapsulated in the inner alginate particles of the fibers. The fibers were freely suspended in calcium chloride solution. Scale bars=200 µm. Panel (b) illustrates bright-field images of an alginate-in-oil-in-alginate fiber where the alginate core particles contain magnetic microparticles, allowing the fiber to be attracted to a magnet (at right), as indicated by the arrow. Scale bars=500 µm. Panels (c)-(d) illustrate encapsulation of live cells in alginate-in-oil-in-alginate fibers. Panel (c) illustrates fibroblast cells growing in the alginate fiber compartment with ferrofluid inside the oil-droplet compartment, 3 days after the initial encapsulation. Live/dead assay was performed using calcein-AM (green fluorescence) and ethidium homodimer-1 (red fluorescence). Panel (d) illustrates *E. coli* cells encapsulated in the oil-in-alginate fibers suspended in Luria-Bertani (LB) growth medium after 3 hours. Scale bars=100 µm.
Figure 8:
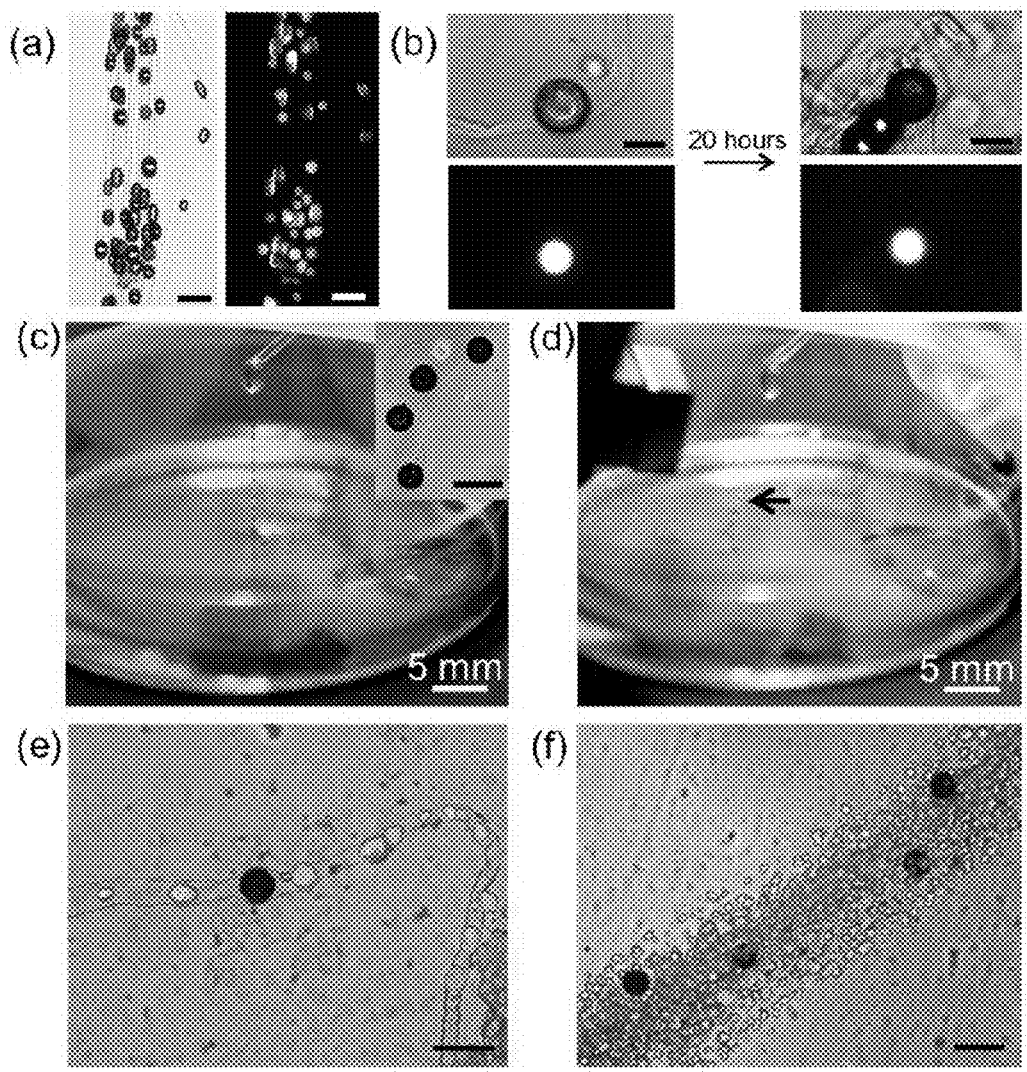
FIG. 8 illustrates exemplary non-limiting compositions in accordance with the present invention. Panel (a) illustrates bright-field and fluorescence images of alginate-in-oil-in-alginate fibers where fluorescent nanoparticles are encapsulated in the inner alginate particles of the fiber. The fibers were spun using a motor. Scale bars=200 µm. Panel (b) illustrates encapsulation of FITC conjugated BSA in the inner alginate particles in the alginate-in-oil-in-alginate fiber composite structure stored in DI water for 20 hours. Scale bars=100 µm. Panel (c) illustrates alginate-in-oil-in-alginate fiber, where the oil compartment contained a ferrofluid, flowing out of the outlet tubing of the microfluidic device. Inset bright field image shows the structure of the magnetic multicompartment fiber. Scale bar=200 As illustrated in panel (d), the fiber was deflected in the direction of a magnet, as indicated by the arrow. Panel (e) illustrates fibroblast cells after 6 days of growing inside the fiber with ferrofluid-oil droplets, forming the cell spheroids. Panel (f) illustrates the finding that cell-encapsulated fibers, spun on the needles using a motor, formed a thin cell-sheet of alginate hydrogel embedded with ferrofluid-oil droplets. Scale bars=200 µm.

A wide variety of cargos can be added to the different compartments of the microfiber. Table 1, FIG. 2 and FIG. 8 illustrate the encapsulation of various materials in the three different microcompartments of the composite fiber. As calcium-crosslinked alginate is hydrophilic and has pore sizes on the order of 10 nm, the heterogeneous composite structure of the fiber is more suitable for storing materials with various sizes and chemistries. Thus, encapsulation of small molecule, macromolecule, and micro- and nano-particulate cargo was investigated, some of which are hydrophobic and others hydrophilic.

As a model particle cargo, 200 nm fluorescent nanoparticles were added to the inner alginate particle to produce fluorescent core microfibers (FIG. 2, panel a, and FIG. 8, panel a). The nanoparticles were clearly encapsulated in the inner particles of the fiber, and were not found elsewhere in the fiber structure. Encapsulation of proteins was demonstrated by adding fluorescein isothiocyanate (FITC) conjugated bovine serum albumin (BSA; molecular weight: 66 kDa) to the alginate particles. FITC-conjugated BSA encapsulated in the inner alginate particle was also protected by the oil layer of the outer droplet compartment, and the fluorescence was observed for at least 20 hours (FIG. 8, panel b).

Similarly, magnetic microparticles of 1 µm diameter were added to the inner alginate particle. The magnetic alginate particles allowed the fiber to respond to an external magnetic field (FIG. 2, panel b), where the multicompartment fiber, suspended in calcium chloride solution, was drawn towards a magnet. The fibers can also exhibit magnetic properties by adding magnetic material to the oil phase. To illustrate this feature, an oil-based ferrofluid, containing 10 nm diameter iron oxide nanoparticles, was incorporated in the oil droplets of the fiber to produce magnetically responsive fibers (FIG. 8, panels c and d).

Example 3

A hydrogel fiber can be used to study three-dimensional cell growth and as a scaffold for tissue engineering. The methods and devices of the present invention allow for incorporating magnetic properties in hydrogels, without having to disperse the magnetic particles in the hydrogel precursors. With that objective, oil-based ferrofluid was added in the oil compartment of the fibers and mammalian cells were grown inside the alginate fiber (FIG. 2, panel c; FIG. 8, panels e and f). The cells, which were randomly dispersed throughout the outer alginate regions of the fiber initially, grew and formed aggregates. Those aggregates continued to increase in size to form large spherical aggregates over the incubation period (FIG. 8, panel e). A live/dead assay showed high viability (94% viability) of the cells after growing for 6 days inside fibers that were freely suspended in cell medium. Since the oil-based ferrofluid was localized only in the oil compartment, very high concentrations of ferrofluid were encapsulated for strong magnetic attraction without affecting the cells in the fiber. Fibers spun with a motor formed a sheet of cells embedded with ferrofluid droplets (FIG. 8, panel f). After 6 days, 84% of the cells grown in the sheet were viable, showing more death of the cells in the middle of the sheet possibly due to a deficiency of oxygen and nutrient transport.

With respect to the use of magnetic particles in the distinct compartments, the fibers can be retrieved and separated from solution using a magnet, which subjects the fibers to less mechanical stress than many other separation methods. So for multistep procedures where the fibers need to be moved to different solutions, such as multiple washing steps, magnetic separation is convenient. Furthermore, the added magnetic functionality suggests that the multicompartment fibers can be utilized in bioseparations and assembly.

Example 4

Figure 3:
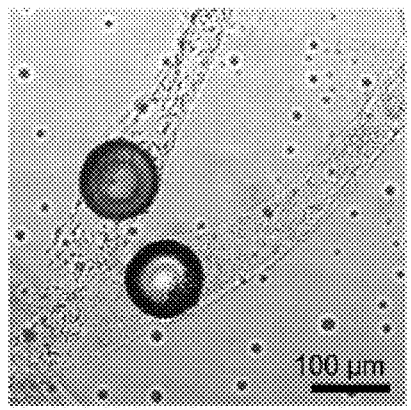
FIG. 3 illustrates a study of the antibacterial effect of eugenol oil on *E. coli* cells within exemplary multicompartment fibers. As illustrated in panel (a), for the alginate fibers containing up to 10% (v/v) eugenol droplets inside, the GFP-expressing *E. coli* cells grew around the oil droplets and covered most of the fibers completely after 15 hours. As illustrated in panel (b), in 20% (v/v) eugenol droplets-in-alginate fibers, the growth of E. coli already slowed down around the oil droplets after 3 hours, and no growth was observed around the rim of the droplets even after 15 hours.
Figure 3:
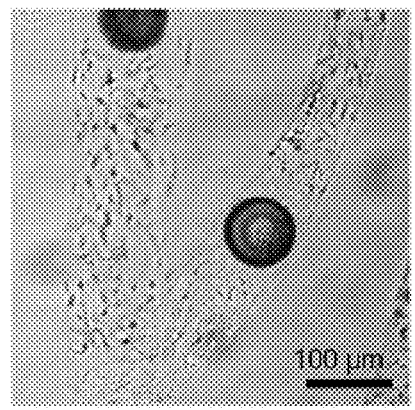
Figure 3:
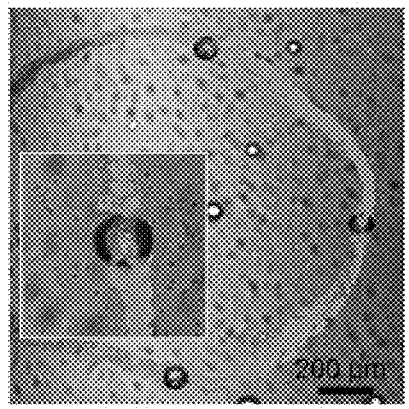
Figure 3:
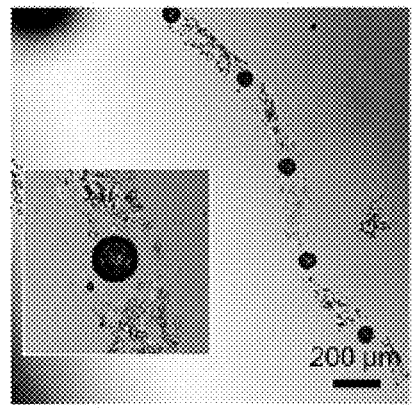
Figure 3:
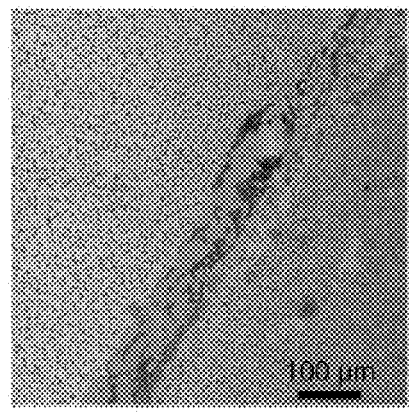
Figure 3:
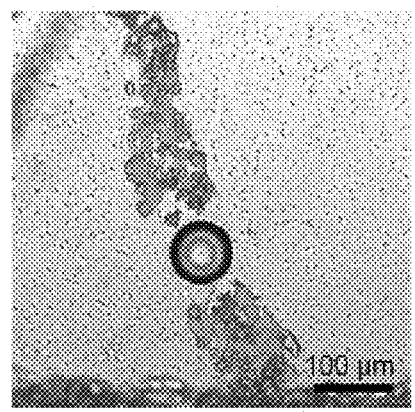
Figure 9:
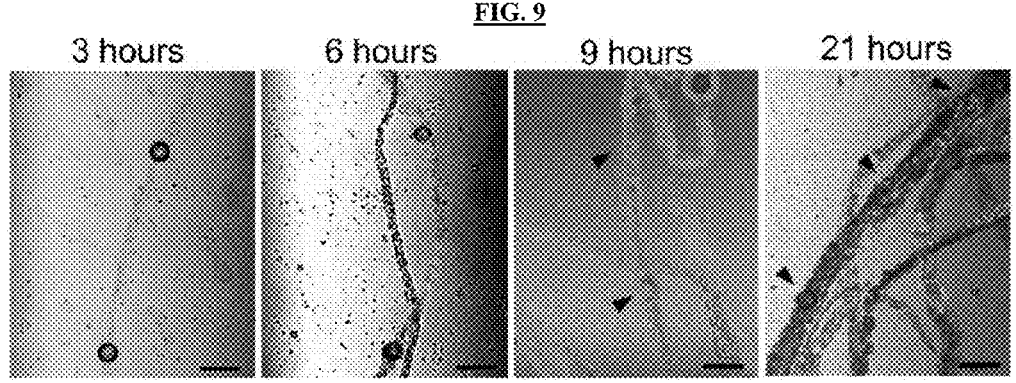
FIG. 9 illustrates growth of GFP-expressing E. Coli around the oil compartment of 2 wt % Span80 (also known as sorbitane monooleate, or sorbitan oleate) in mineral oil in the alginate fiber. Black arrows indicate where the oil droplets were inside the fiber. Scale bars=200 µm.

The growth of bacterial cells, Escherichia coli (E. coli), in the oil droplet-in-alginate fibers (FIG. 2, panel d) was also tested. The E. coli cells encapsulated in the fibers were suspended in the LB medium for 21 hours, and grew well inside the fibers where they completely surrounded the oil droplets (FIG. 9). The oil microcompartments of the fiber can be used to encapsulate hydrophobic drugs or antibacterial chemicals to test their effects on the cells. For example, eugenol is an antibacterial compound found in clove oil. Eugenol was dissolved in the oil compartment, in a solution comprising mineral oil with 5% (v/v) undecanol and 2 wt % Span 80. The undecanol was used to aid the mixing of eugenol oil with the mineral oil. Qualitatively, a reduction in the overall growth rate of E. coli was observed in the presence of the eugenol-oil droplets inside the fiber, at eugenol concentrations up to 10% (v/v). However, no significant difference in the cell growth was around the eugenol droplets (FIG. 3, panel a), compared with the cells around oil droplets with no eugenol (FIG. 9). At 20% (v/v) eugenol-oil droplets, a significant decrease in the cell population around the oil droplets was observed (FIG. 3, panel b). Thus, multicompartment fibers carrying either oil or water-based droplets can be used to study the effect of drugs on cells, even with chemicals of low solubility in water. Also, the encapsulated droplets provide another method to localize and pattern multiple cell types inside the fiber according to the attractive or repulsive characteristics of the cells towards the contents of the droplets.

Example 5

Figure 10:
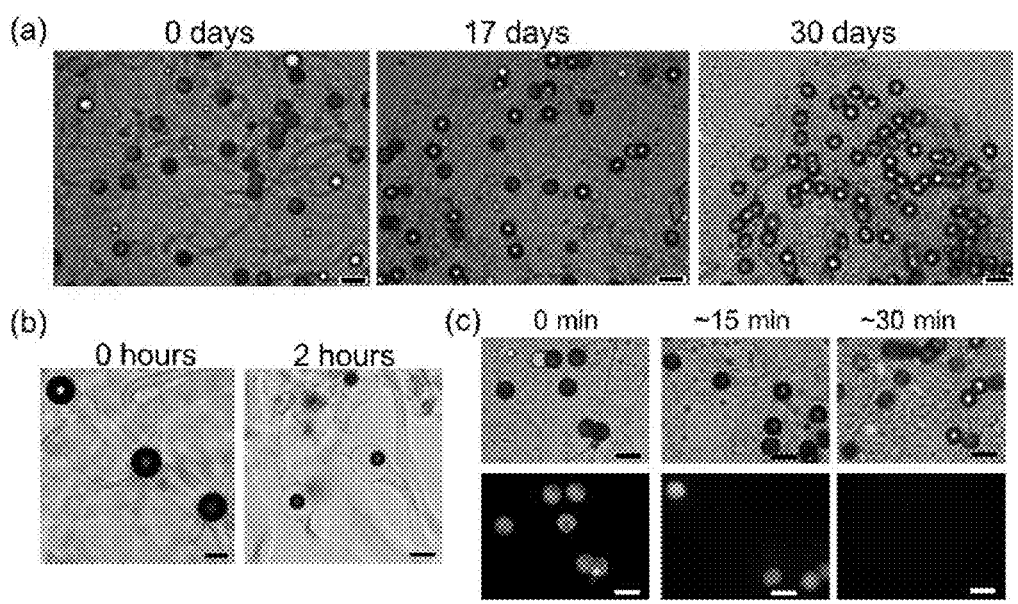
FIG. 10 illustrates non-limiting examples of alginate-in-oil-in alginate fibers. Panel (a) illustrates overlaid bright-field and fluorescence images of alginate-in-Nile Red oil-in-alginate fibers suspended in water showing the long-term stability of the multicomponent fibers. Scale bars=200 µm. Panel (b) illustrates that the oil compartment dissolved and shrank in volume in water when more soluble oil, such as eugenol, was used as the oil compartment instead of mineral oil. Scale bars=100 µm. Panel (c) illustrates bright-field and fluorescence images of alginate-in-Nile Red oil-in-alginate fibers in a water/ethanol solution, where the presence of ethanol caused the contents of the oil compartment to escape the fiber as shown by the loss of dye from the oil compartments. Scale bars=200 µm.

The multicompartment fibers of the present invention exhibited long-term stability when stored in water. Alginate-in-oil-in-alginate fibers were prepared, and stored in deionized (DI) water. The fibers were monitored periodically over a 30 days period, and no significant changes in the fiber structure were observed during this time (FIG. 10, panel a). The fiber compartments—inner alginate particles, oil droplets, and the alginate fiber itself—remained intact during a month of storage in DI water, showing no evidence of droplet coalescence. Thus, the multicompartment fibers can be used as a stable storage system of the alginate particles or oil droplets.

The previously described experiments were conducted with mineral oil as the oil phase. However, when oil with higher miscibility in water, such as eugenol, was used (solubility in water, 2.46 mg·mL$^{-1}$), the fiber structure change over time. Eugenol droplets (100% eugenol) embedded in the fiber dissolve in water, shrinking from 120 µm to 50 µm in diameter over a period of 2 hours (FIG. 10, panel b). Depending on properties such as size and hydrophilic/hydrophobic affinity, the materials to be encapsulated in the droplet compartment can be stably stored or released over time from the fiber.

Figure 4:
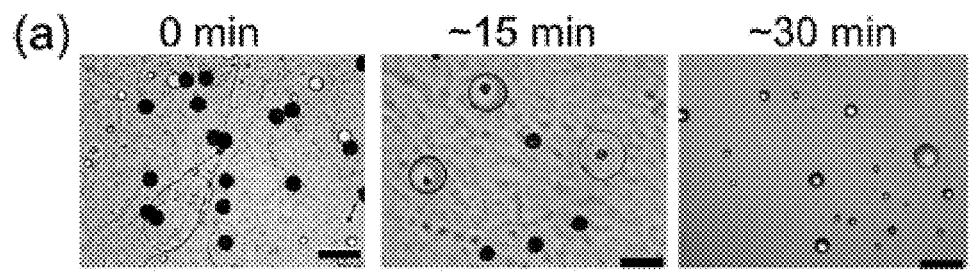
FIG. 4 illustrates the stability and dissolution studies of exemplary multicompartment fibers in (panels (a)-(b)) a solution of sodium citrate and (panel (c)) a solution of ethanol in water. Panel (a) illustrates bright-field images of alginate-in-oil-in-alginate fibers suspended in a solution of sodium citrate showing the dissolution of the alginate hydrogel, which leaves behind the oil droplets. Panel (b) illustrates bright-field images of alginate-in-ferrofluid oil-in-alginate fibers suspended in a solution of sodium citrate, showing the partial dissolution of an inner alginate particle in an oil droplet (indicated by the red arrow), where the oil droplet was released from the dissolving alginate fiber, and then the inner alginate particle broke open. After relatively long times, the broken inner alginate particle dissolved completely leaving only oil droplets. Panel (c) illustrates comparison of green NP alginate-in-Nile red oil-in-alginate fibers left for 18 hours in DI water (left) and water/ethanol solution (right), showing the loss of the oil solution containing Nile red dye, in the case of the ethanol but not in the case of pure water. The fluorescent nanoparticles in the inner alginate particles remained intact in the presence of ethanol. Scale bars=200 µm.
Figure 4:
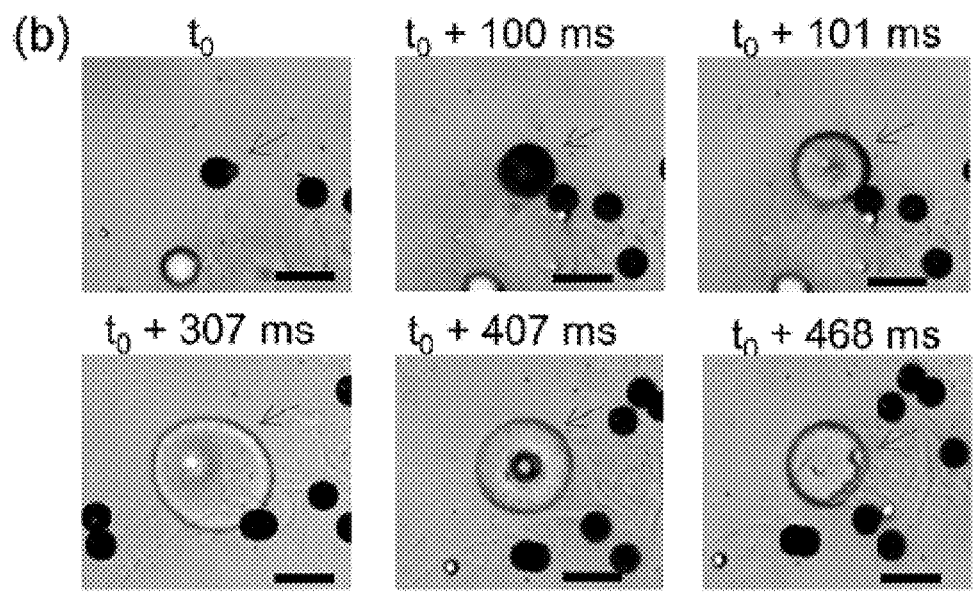
Figure 4:
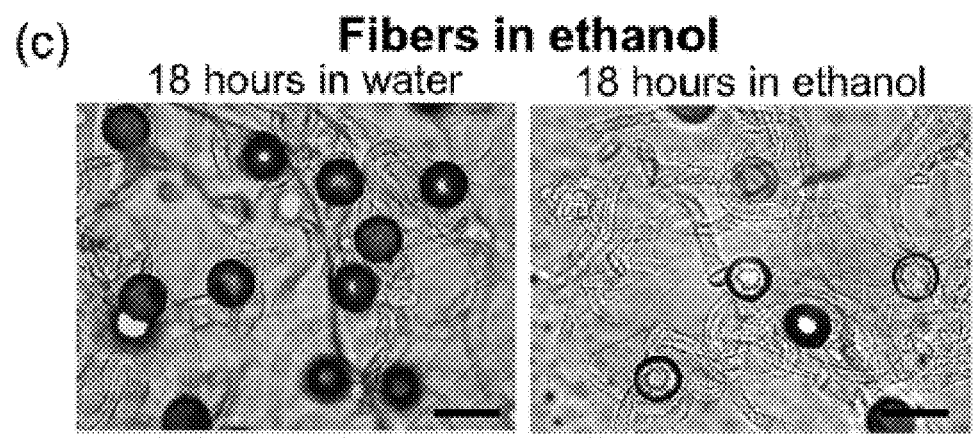

Upon demand, the droplet compartment stored inside the fiber can also be released and recovered. Calcium alginate gels can be dissolved using chelating agents, such as sodium citrate, where the citrate anions remove the calcium cations from the alginate gel, thereby uncrosslinking the gel. In order to demonstrate the release of the oil compartments, an aqueous solution of sodium citrate was added to a suspension of the multicompartment fibers of the present invention in DI water. The alginate gel that composes the main body of the fibers began to dissolve, releasing the oil droplets, which then floated to the surface of the solution (FIG. 4, panel a). In the early stages of dissolution, the inner alginate particles in the oil droplets remained intact and were visible in the released oil droplets. The inner alginate particles did eventually dissolve leaving only oil droplets in solution. Without wishing to be limited by any theory, there was an intermediate step in the dissolution of some of the inner alginate particles (FIG. 4, panel b); upon release of the oil droplets from the fiber, the intact inner alginate particles, which appeared to have shell structures, first ruptured and broke into pieces, and then eventually dissolved completely.

To study the effect of the hydrophobic chemical on the cells, a lipophilic compound such as eugenol, which has slight solubility in water, was used. If the miscibility of the compounds in the oil droplets is too low to cause passive release in pure water, a suitable solvent, such as dimethylsulfoxide (DMSO), may be added at low concentrations to aid in the removal of the contents of the oil microcompartments of the fibers. For non-biological applications, stronger organic solvents may be used.

As a non-limiting example, ethanol was used to affect oil phase removal. The oil phase, which was a solution of mineral oil, 5% (v/v) undecanol, and 2 wt % Span 80 surfactant, was slightly miscible with ethanol, and thus was able to slowly escape the oil microcompartments in the fiber in the presence of ethanol. Alginate-in-oil-in-alginate fibers were prepared with 0.3 mg·mL$^{-1}$ of a lipophilic fluorescent dye, Nile Red, in the oil droplets, and green fluorescent nanoparticles of 190 nm diameter in the inner alginate particles; one fiber sample was immersed in water, and the second fiber sample was immersed in an ethanol/water solution. The red fluorescence of the Nile Red dye in the oil microcompartments was observed in the fiber immersed over 18 hours in water (FIG. 4, panel c, left). However, upon addition of ethanol, the red fluorescence in the oil droplets of the fibers became less intense and appeared more diffuse over time (FIG. 10, panel c). After a longer time, no further red fluorescence was observed in the fibers, which indicates that the lipophilic dye partitioned from the oil microcompartments into the suspending solution because of the presence of ethanol. In addition, the oil microcompartments lost their spherical shape as their contents were removed (FIG. 4, panel c, right). Green fluorescence from the nanoparticles encapsulated in the inner alginate particles of the fibers was still observed, indicating that the core structures were unaffected by the presence of ethanol. Without wishing to be limited by any theory, materials that are already encapsulated inside the inner alginate particles remain inside as long as the material has lower affinity towards the solvents. Depending on the solvents suitable for the specific application, materials may be encapsulated either in the aqueous phase or the oil phase; as there is a broad range available for material selection. This highlights the fact that the multicompartment fibers of the present invention can be applied towards various biological and non-biological applications.

Example 6

The present invention includes fiber microstructures such as a core-shell droplet-in-fiber structure. In such structure, there are three microcompartments, wherein the middle hydrophobic compartment is a continuous core that spans the length of the fiber. In certain embodiments, higher loading capacities are achieved due to the larger hydrophobic compartment of the fiber core, as opposed to the hydrophobic droplet phase of the double-emulsion-in-fiber structure.

Figure 16:
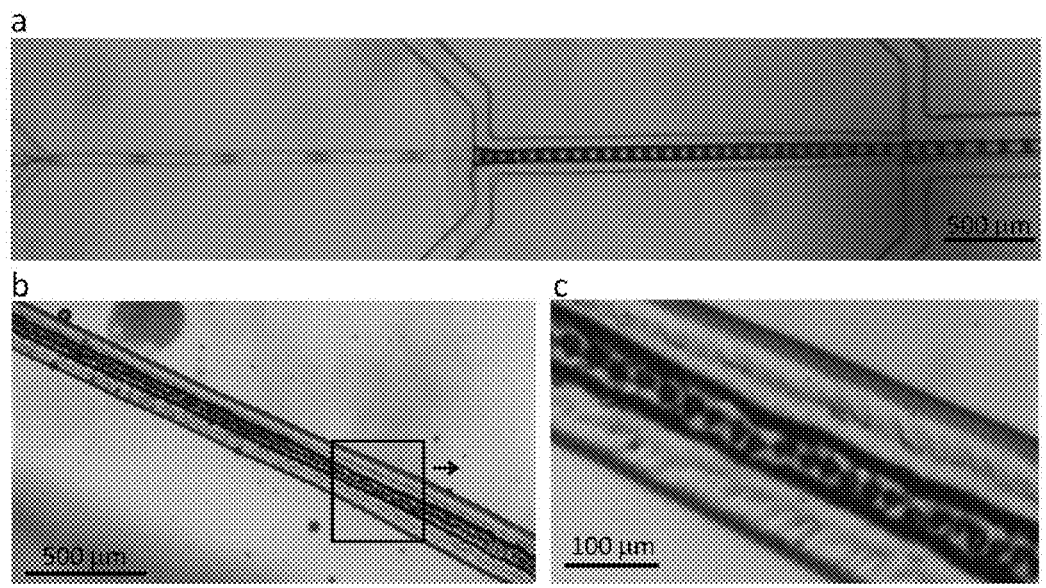
FIG. 16 illustrates the formation of core-shell droplet-in-fiber fibers. Panel a illustrates bright-field microscopy image of microfluidic device during the production of the core-shell droplet-in-fiber fibers, where water droplets were flowed into a polymerizable hydrophobic monomer solution, which was then flowed into a polymerizable hydrophilic monomer solution. The monomer solutions were polymerized when exposed to UV light in the main channel. Panel b illustrates bright-field microscopy image of a core-shell droplet-in-fiber structure showing three compartments. Panel c illustrates higher magnification view of the fiber structure.

Water droplets in a hydrophobic monomer solution, composed of 60 vol % trimethylolpropane triacrylate (TMPTA), 20 vol % eugenol and 20 vol % Darocur 1173 photoinitiator, were generated at the first flow-focusing junction. The TMPTA solution, containing water droplets, was flowed into a hydrophilic monomer solution, composed of 54 vol % poly(ethylene glycol) diacrylate) (PEG-DA; MW=575 g/mol), 42 vol % water and 4 vol % photoinitiator at the second flow-focusing junction. Because the interfacial tension between the TMPTA and PEG monomer solutions was very low, the TMPTA jet remained as a stable stream within the PEG solution, without significant breaks. The three phases (water, TMPTA and PEG) were flowed into a non-reactive oil solution, composed of hexadecane with 4 vol % Span 80, at the third junction. Again, as the interfacial tension between the oil and PEG phases was very low, the streams did not fragment into droplets. FIG. 16, panel a, illustrates various solutions flowing in the microfluidic device. Once in the main channel, the solutions were exposed to UV light, and converted to a solid fiber, composed of a hydrophilic shell with a continuous hydrophobic core containing water droplets (FIG. 16, panels b-c).

Example 7

Figure 17:
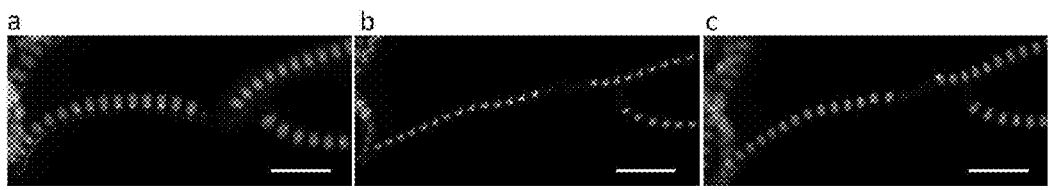
FIG. 17 illustrates fluorescence microscopy images of droplet-in-fibers, where the aqueous droplets contain rhodamine labeled dextran. As illustrated in panel a, the fibers were swollen in 1 wt % tween 80 solution, where the concentration of dextran was measured to be 2.4 wt %, then (panel b) the solution was changed to 20 wt % $PEG_{8000}$ where the aqueous compartments shrunk over 21 hours and the concentration of dextran was measured to be 3.6 wt %. As illustrated in panel c, the solution was again changed to 1 wt % tween 80, where the aqueous compartments were swollen to recover almost the same concentration as in panel a, after approximately 27 hours, 2.6 wt % dextran. The concentration of dextran in the fibers was measured from the calibrated fluorescence intensity. The fibers produced in this figure were prepared by pulsed UV light, so that they were of short uniform length. Scale bars=500 μm.

Hydrophobic droplet-in-fibers were prepared according to the methods of the present invention. Water droplets were embedded in a UV-polymerized hydrophobic fiber using the microfluidic method of the present invention, using two flow-focusing junctions. Aqueous droplets were first formed in a hydrophobic monomer solution of poly(ethylene glycol) diacrylate (PEG-DA, MW=250 g/mol) with 4 vol % photoinitiator at the first junction, then the water-PEG phases were sheathed by a non-reactive oil phase, composed of hexadecane with 10 vol % Span 80 at the second flow-focusing junction. The PEG-DA jet was crosslinked when exposed to UV light in the main channel. Hydrophobic fibers containing aqueous droplets were thus produced. Various compounds were dissolved into the aqueous droplets, including a food grade dye, erioglaucine, rhodamine labeled dextran and the protein, xylanase. The dissolved compounds remained within the aqueous compartments. However, water and other small molecules diffused in and out of the microcompartments depending on the composition of the suspending medium. For example, as shown in FIG. 17, when the fibers are suspended in an aqueous solution containing 1 wt % Tween 80, the aqueous compartments appeared swollen due to influx of water, but appear deflated when suspended in a 20 wt % solution of poly(ethylene glycol) (MW=8000 g/mol). This indicates that the concentration of the dissolved compound can be changed within the fiber. The ability of varying the osmotic property of the aqueous compartment may be used in applications that require controlled concentration changes, such as protein crystallization, as well as in sensing applications and controlled release applications.

Figure 18:
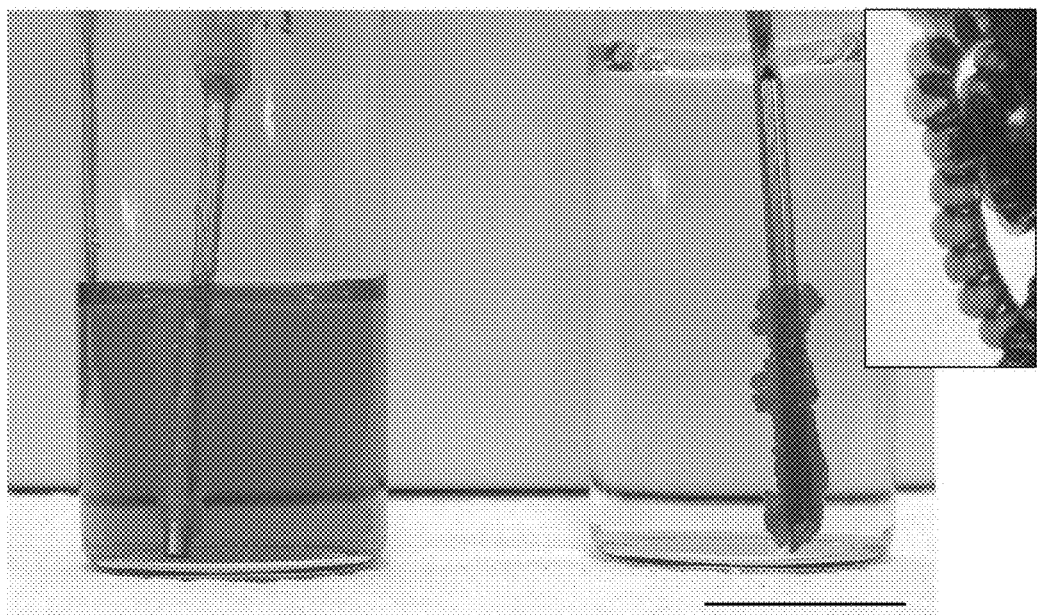
FIG. 18 illustrates hydrophobic droplet-in-fibers wrapped around needles immersed in water. On the left, the fiber precursor solution contained 76 vol % $PEG_{250}DA$, 20 vol % $PEG_{700}DA$ and 4 vol % photoinitiator. On the right, the fiber precursor solution contained 96 vol % $PEG_{250}DA$ and 4 vol % photoinitiator. Both fibers contained aqueous droplets with 1 wt % erioglaucine (blue dye). The presence of the higher molecular weight monomer allowed the blue dye to diffuse out of the fiber. The inset image shows a higher magnification view of the fibers containing only $PEG_{250}DA$. Scale bar=1 cm.

Further, if the composition of the fiber precursor solution was change, for example, by adding a small amount of longer chain PEG-DA monomer, the permeability of the fiber is varied, allowing for the release of the dissolved compounds from the fiber (FIG. 18).

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the present invention. The appended claims are intended to be construed to include all such embodiments and equivalent variations.

What is claimed is:

1. A method of preparing a microfiber, the method comprising the steps of:
   (a) providing a microfluidic device comprising:
      a first microfluidic duct for delivering a first fluid;
      a second microfluidic duct for delivering a second fluid, the second fluid being immiscible with the first fluid, wherein the first microfluidic duct opens into the second microfluidic duct and forms a first fluidic junction therewith;
      a third microfluidic duct that is in fluid communication with the first fluidic junction and is wettable by the second fluid;
      a fourth microfluidic duct for delivering a third fluid, wherein the third microfluidic duct opens into the fourth microfluidic duct and forms a second fluidic junction therewith;
   (b) delivering a first fluid to the first microfluidic duct and a second fluid to the second microfluidic duct, whereby a first emulsion comprising the first fluid into the second fluid is formed within or in the proximity of the first fluidic junction; and
   (c) delivering a third fluid to the fourth microfluidic duct, whereby a mixture of the third fluid and the first emulsion is formed within or in the proximity of the second fluidic junction,
wherein the third fluid is a second continuous phase,
wherein an outlet is in fluid communication with the second fluidic junction, and
wherein the microfiber is formed within or in the proximity of the outlet of the second fluidic junction.

2. The method of claim 1, wherein the first fluidic junction is selected from the group consisting of a flow-focusing junction and at-junction.

3. The method of claim 1, wherein the second fluidic junction is a flow-focusing junction.

4. The method of claim 1, wherein the third microfluidic duct is at least partially coated with a polymer that is wettable by the second fluid.

5. The method of claim 1, wherein the microfiber comprises a matrix material; wherein the microfiber further comprises a plurality of droplets embedded in the matrix material along the length thereof;
   wherein each one of the plurality of droplets independently comprises the first emulsion, which comprises a first droplet phase within a second droplet phase; and
   wherein the matrix material of the microfiber is insoluble in the second droplet phase of each one of the plurality of droplets.

6. The method of claim 5, wherein the matrix material has a composition that does not vary substantially along a length of the microfiber.

7. The method of claim 5, wherein the matrix material has a composition that varies along a length of the microfiber.

8. The method of claim 5, wherein each one of the plurality of the droplets has a like composition.

9. The method of claim 5, wherein at least one of the plurality of droplets has a first composition, and at least one other of the plurality of droplets has a second composition, the first composition being different from the second composition.

10. The method of claim 5, wherein the matrix material further comprises at least one agent selected from the group consisting of a cell, tissue, filler, therapeutic drug, chemoattractant, biocide, ion, peptide, protein, nucleic acid, magnetic compound, and detectable probe.

11. The method of claim 5, wherein at least one of the plurality of droplets further comprises at least one agent selected from the group consisting of a cell, tissue, filler, therapeutic drug, chemoattractant, biocide, ion, peptide, protein, nucleic acid, magnetic compound, and detectable probe.

12. The method of claim 5, wherein at least one selected from the group consisting of the matrix material and at least one of the plurality of droplets comprises a magnetic compound.

13. The method of claim 5, wherein the matrix material of the microfiber is hydrophilic and the second droplet phase of each one of the plurality of droplets is hydrophobic.

14. The method of claim 5, wherein the matrix material of the microfiber is hydrophobic and the second droplet phase of each one of the plurality of droplets is hydrophilic.

15. The method of claim 5, wherein the first droplet phase of at least one of the plurality of droplets comprises a solid.

16. The method of claim 5, wherein within at least one of the plurality of droplets the first droplet phase comprises a first agent and the second droplet phase comprises a second agent, the second agent having at least one property selected from the group consisting of solubility and chemical compatibility that is distinct from that of the first agent.

17. The method of claim 5, wherein the matrix material of the microfiber is biodegradable.

18. The method of claim 1,
   wherein the microfluidic device further comprises:
   a fifth microfluidic duct that originates from the second fluidic junction and is wettable by the third fluid;
   a sixth microfluidic duct for delivering a fourth fluid, wherein the fifth microfluidic duct opens into the sixth microfluidic duct and forms a third fluidic junction therewith; and
   an outlet that is in fluid communication with the third fluidic junction;

wherein the mixture of the third fluid and the first emulsion is comprised in a second emulsion; and wherein the method further comprises:

(d) delivering a fourth fluid to the sixth microfluidic duct, whereby a mixture of the fourth fluid and the second emulsion is formed; and (e) allowing the microfiber to form within or in the proximity of the outlet of the third fluidic junction.

19. The method of claim 18, wherein the first and second fluidic junctions are independently selected from the group consisting of a flow-focusing junction and at-junction.

20. The method of claim 18, wherein the third fluidic junction is a flow-focusing junction.

21. The method of claim 18, wherein the third microfluidic duct is at least partially coated with a polymer that is wettable by the second fluid.

22. The method of claim 18, wherein the fifth microfluidic duct is at least partially coated with a polymer that is wettable by the third fluid.

23. The method of claim 18, wherein the microfiber comprises a matrix material;

wherein the microfiber further comprises a plurality of droplets embedded in the matrix material along the length thereof;

wherein each one of the plurality of droplets independently comprises the second emulsion, which comprises a first droplet phase within a second droplet phase, wherein the first droplet phase comprises the first emulsion; and wherein the matrix material of the microfiber is insoluble in the second droplet phase of each one of the plurality of droplets.

24. The method of claim 23, wherein the matrix material has a composition that does not vary substantially along a length of the microfiber.

25. The method of claim 23, wherein the matrix material has a composition that varies along a length of the microfiber.

26. The method of claim 23, wherein each one of the plurality of the droplets has a like composition.

27. The method of claim 23, wherein at least one of the plurality of droplets has a first composition, and at least one other of the plurality of droplets has a second composition, the first composition being different from the second composition.

28. The method of claim 23, wherein the matrix material further comprises at least one agent selected from the group consisting of a cell, tissue, filler, therapeutic drug, chemoattractant, biocide, ion, peptide, protein, nucleic acid, magnetic compound, and detectable probe.

29. The method of claim 23, wherein at least one of the plurality of droplets further comprises at least one agent selected from the group consisting of a cell, tissue, filler, therapeutic drug, chemoattractant, biocide, ion, peptide, protein, nucleic acid, magnetic compound, and detectable probe.

30. The method of claim 23, wherein at least one selected from the group consisting of the matrix material and at least one of the plurality of droplets comprises a magnetic compound.

31. The method of claim 23, wherein the matrix material of the microfiber is hydrophilic and the second droplet phase of each one of the plurality of droplets is hydrophobic.

32. The method of claim 23, wherein the matrix material of the microfiber is hydrophobic and the second droplet phase of each one of the plurality of droplets is hydrophilic.

33. The method of claim 23, wherein the first droplet phase of at least one of the plurality of droplets comprises a solid.

34. The method of claim 23, wherein within at least one of the plurality of droplets the first droplet phase comprises a first agent and the second droplet phase comprises a second agent, the second agent having at least one property selected from the group consisting of solubility and chemical compatibility that is distinct from that of the first agent.

35. The method of claim 23, wherein the matrix material of the microfiber is biodegradable.

* * * * *